(12) United States Patent
Pratt et al.

(10) Patent No.: US 12,285,246 B2
(45) Date of Patent: Apr. 29, 2025

(54) HEART AND LUNG MONITORING WITH COHERENT SIGNAL DISPERSION

(71) Applicant: University of Notre Dame du Lac, South Bend, IN (US)

(72) Inventors: Thomas G. Pratt, Niles, MI (US); Jeffrey G. Mueller, South Bend, IN (US); Robert D. Kossler, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 11 days.

(21) Appl. No.: 18/225,335

(22) Filed: Jul. 24, 2023

(65) Prior Publication Data

US 2024/0000333 A1 Jan. 4, 2024

Related U.S. Application Data

(63) Continuation of application No. 16/483,022, filed as application No. PCT/US2018/016927 on Feb. 5, (Continued)

(51) Int. Cl.
*A61B 5/05* (2021.01)
*A61B 5/00* (2006.01)
(Continued)

(52) U.S. Cl.
CPC .............. *A61B 5/05* (2013.01); *A61B 5/1102* (2013.01); *A61B 5/1126* (2013.01); *A61B 5/113* (2013.01);
(Continued)

(58) Field of Classification Search
CPC ................................. A61B 5/05; A61B 5/7257
See application file for complete search history.

(56) References Cited

U.S. PATENT DOCUMENTS

| 4,958,638 A | 9/1990 | Sharpe et al. |
| 5,235,340 A | 8/1993 | Shea |

(Continued)

FOREIGN PATENT DOCUMENTS

| JP | 4250480 B | 1/2009 |
| JP | 5825557 B2 | 10/2015 |

(Continued)

OTHER PUBLICATIONS

O. Boric-Lubecke et al, "Doppler Radar Sensing of Multiple Subjects in Single and Multiple Antenna Systems", International Conference on Telecommunication in Modern Satellite, Cable and Broadcasting Services (TELSIKS), vol. 1, pp. 7-11, 2005 (Year: 2005).*

(Continued)

*Primary Examiner* — Jeffrey G Hoekstra
*Assistant Examiner* — Nyrobi Celestine
(74) *Attorney, Agent, or Firm* — ICE MILLER LLP

(57) ABSTRACT

Methods and systems for sensing a physiological characteristic of a subject. At least one receiver antenna can be provided in proximity to a portion of the subject's body to obtain at least one receiver signal resulting from at least one transmitter signal that has propagated to the receiver antenna and has been reflected, diffracted, scattered, or transmitted by or through the portion of the subject's body. One or more coherent signal pairs can be formed. Then, amplitude and phase information of a plurality of frequency components for each signal pair can be determined. A set of comparison values can be determined for each signal pair by comparing respective frequency component phases and respective frequency component amplitudes of the signals. Physiological characteristics of the subject can then be determined from these comparison values.

40 Claims, 15 Drawing Sheets

Related U.S. Application Data 2018, now abandoned, which is a continuation-in-part of application No. 14/936,536, filed on Nov. 9, 2015, now Pat. No. 10,605,841.

(60) Provisional application No. 62/454,437, filed on Feb. 3, 2017.

(51) Int. Cl.
| | |
|---|---|
| *A61B 5/02* | (2006.01) |
| *A61B 5/021* | (2006.01) |
| *A61B 5/024* | (2006.01) |
| *A61B 5/08* | (2006.01) |
| *A61B 5/091* | (2006.01) |
| *A61B 5/11* | (2006.01) |
| *A61B 5/113* | (2006.01) |

(52) U.S. Cl.
CPC .......... *A61B 5/6891* (2013.01); *A61B 5/6892* (2013.01); *A61B 5/02007* (2013.01); *A61B 5/02028* (2013.01); *A61B 5/021* (2013.01); *A61B 5/02444* (2013.01); *A61B 5/0816* (2013.01); *A61B 5/091* (2013.01)

(56) References Cited

U.S. PATENT DOCUMENTS

| | | | | |
|---|---|---|---|---|
| 5,920,595 | A | 7/1999 | Iwamatsu | |
| 8,206,324 | B2* | 6/2012 | Kurono | G01M 11/083 600/595 |
| 9,970,955 | B1* | 5/2018 | Homyk | A61B 5/0261 |
| 2003/0220749 | A1* | 11/2003 | Chen | A61B 5/445 702/31 |
| 2004/0249257 | A1 | 12/2004 | Tupin et al. | |
| 2005/0171438 | A1* | 8/2005 | Chen | G01B 9/0201 600/425 |
| 2005/0286665 | A1 | 12/2005 | Resheff et al. | |
| 2007/0047678 | A1 | 3/2007 | Sibecas et al. | |
| 2008/0045832 | A1 | 2/2008 | Mcgrath | |
| 2008/0074307 | A1 | 3/2008 | Boric-Lubecke et al. | |
| 2009/0015832 | A1 | 1/2009 | Popovic et al. | |
| 2009/0203972 | A1 | 8/2009 | Heneghan et al. | |
| 2010/0087738 | A1 | 4/2010 | Fornwalt et al. | |
| 2010/0152600 | A1 | 6/2010 | Droitcour et al. | |
| 2010/0222022 | A1 | 9/2010 | Fujita et al. | |
| 2010/0241010 | A1 | 9/2010 | Lin et al. | |
| 2010/0256462 | A1 | 10/2010 | Rappaport et al. | |
| 2010/0292559 | A1 | 11/2010 | Hannemann et al. | |
| 2013/0332115 | A1* | 12/2013 | Pratt | G01N 22/04 702/189 |
| 2014/0316261 | A1 | 10/2014 | Lux et al. | |
| 2015/0223722 | A1 | 8/2015 | Wyeth et al. | |
| 2015/0223733 | A1 | 8/2015 | Al-Alusi | |
| 2016/0015352 | A1 | 1/2016 | Brown et al. | |
| 2016/0022145 | A1 | 1/2016 | Mostov | |
| 2018/0081030 | A1 | 3/2018 | Mcmahon et al. | |

FOREIGN PATENT DOCUMENTS

| | | |
|---|---|---|
| JP | 5843430 B | 11/2015 |
| JP | 2016046039 A | 4/2016 |
| JP | 2020505179 A | 2/2020 |
| WO | 2009124297 A1 | 10/2009 |
| WO | 2016170005 A1 | 10/2016 |

OTHER PUBLICATIONS

C. Li et al, "Complex signal demodulation and random body movement cancellation techniques for non-contact vital sign detection", 2008 IEEE MTT-S International Microwave Symposium Digest, pp. 567-570, 2008 (Year: 2008).*

Search Report and Written Opinion, dated May 11, 2018, issued in PCT/US2018/016927.

International Preliminary Report on Patentability dated Aug. 6, 2019, issued in PCT/US2018/016927.

Extended European Search Report dated Mar. 5, 2021, ssued in EP18747822.7.

Samardzja et al., "Applications of MIMO Techniques to Sensing of Cardiopulmonary Activity," 4 pgs.

Office Action (English Translation) dated Dec. 13, 2021, issued in Japanese Patent Application No. 2019-542226.

Office Action (English Translation) dated Sep. 5, 2022, issued in Japanese Patent Application No. 2019-542226.

\* cited by examiner

|   | Signal Pairs | |
|---|---|---|
| 1 | $S_{R1}$ | $S_{R2}$ |
| 2 | $S_{T1}$ | $S_{R1}$ |
| 3 | $S_{T1}$ | $S_{R2}$ |

*FIG. 3B*

|   | Signal Pairs | |
|---|---|---|
| 1 | $S_{R1u}$ | $S_{R1v}$ |
| 2 | $S_{R2u}$ | $S_{R2v}$ |
| 3 | $S_{R1u}$ | $S_{R2u}$ |
| 4 | $S_{R1u}$ | $S_{R2v}$ |
| 5 | $S_{R1v}$ | $S_{R2u}$ |
| 6 | $S_{R1v}$ | $S_{R2v}$ |
| 7 | $S_{T1}$ | $S_{R1u}$ |
| 8 | $S_{T1}$ | $S_{R1v}$ |
| 9 | $S_{T1}$ | $S_{R2u}$ |
| 10 | $S_{T1}$ | $S_{R2v}$ |

*FIG. 4B*

| | Signal Pairs | | | | Signal Pairs | |
|---|---|---|---|---|---|---|
| 1 | $S_{R1u}^{T1x}$ | $S_{R1v}^{T1x}$ | 25 | $S_{R2v}^{T1x}$ | $S_{R1u}^{T1y}$ |
| 2 | $S_{R2u}^{T1x}$ | $S_{R2v}^{T1x}$ | 26 | $S_{R2v}^{T1x}$ | $S_{R1v}^{T1y}$ |
| 3 | $S_{R1u}^{T1x}$ | $S_{R2u}^{T1x}$ | 27 | $S_{R2v}^{T1x}$ | $S_{R2u}^{T1y}$ |
| 4 | $S_{R1u}^{T1x}$ | $S_{R2v}^{T1x}$ | 28 | $S_{R2v}^{T1x}$ | $S_{R2v}^{T1y}$ |
| 5 | $S_{R1v}^{T1x}$ | $S_{R2u}^{T1x}$ | | | |
| 6 | $S_{R1v}^{T1x}$ | $S_{R2v}^{T1x}$ | 29 | $S_{T1x}$ | $S_{R1u}^{T1x}$ |
| | | | 30 | $S_{T1x}$ | $S_{R1v}^{T1x}$ |
| 7 | $S_{R1u}^{T1y}$ | $S_{R1v}^{T1y}$ | 31 | $S_{T1x}$ | $S_{R2u}^{T1x}$ |
| 8 | $S_{R2u}^{T1y}$ | $S_{R2v}^{T1y}$ | 32 | $S_{T1x}$ | $S_{R2v}^{T1x}$ |
| 9 | $S_{R1u}^{T1y}$ | $S_{R2u}^{T1y}$ | | | |
| 10 | $S_{R1u}^{T1y}$ | $S_{R2v}^{T1y}$ | 33 | $S_{T1x}$ | $S_{R1u}^{T1y}$ |
| 11 | $S_{R1v}^{T1y}$ | $S_{R2u}^{T1y}$ | 34 | $S_{T1x}$ | $S_{R1v}^{T1y}$ |
| 12 | $S_{R1v}^{T1y}$ | $S_{R2v}^{T1y}$ | 35 | $S_{T1x}$ | $S_{R2u}^{T1y}$ |
| | | | 36 | $S_{T1x}$ | $S_{R2v}^{T1y}$ |
| 13 | $S_{R1u}^{T1x}$ | $S_{R1u}^{T1y}$ | | | |
| 14 | $S_{R1u}^{T1x}$ | $S_{R1v}^{T1y}$ | 37 | $S_{T1y}$ | $S_{R1u}^{T1x}$ |
| 15 | $S_{R1u}^{T1x}$ | $S_{R2u}^{T1y}$ | 38 | $S_{T1y}$ | $S_{R1v}^{T1x}$ |
| 16 | $S_{R1u}^{T1x}$ | $S_{R2v}^{T1y}$ | 39 | $S_{T1y}$ | $S_{R2u}^{T1x}$ |
| | | | 40 | $S_{T1y}$ | $S_{R2v}^{T1x}$ |
| 17 | $S_{R1v}^{T1x}$ | $S_{R1u}^{T1y}$ | | | |
| 18 | $S_{R1v}^{T1x}$ | $S_{R1v}^{T1y}$ | 41 | $S_{T1y}$ | $S_{R1u}^{T1y}$ |
| 19 | $S_{R1v}^{T1x}$ | $S_{R2u}^{T1y}$ | 42 | $S_{T1y}$ | $S_{R1v}^{T1y}$ |
| 20 | $S_{R1v}^{T1x}$ | $S_{R2v}^{T1y}$ | 43 | $S_{T1y}$ | $S_{R2u}^{T1y}$ |
| | | | 44 | $S_{T1y}$ | $S_{R2v}^{T1y}$ |
| 21 | $S_{R2u}^{T1x}$ | $S_{R1u}^{T1y}$ | | | |
| 22 | $S_{R2u}^{T1x}$ | $S_{R1v}^{T1y}$ | | | |
| 23 | $S_{R2u}^{T1x}$ | $S_{R2u}^{T1y}$ | | | |
| 24 | $S_{R2u}^{T1x}$ | $S_{R2v}^{T1y}$ | | | |

*FIG. 5D*

HEART AND LUNG MONITORING WITH COHERENT SIGNAL DISPERSION

INCORPORATION BY REFERENCE TO ANY PRIORITY APPLICATIONS

This application is a continuation of U.S. Ser. No. 16/483,022, filed Aug. 1, 2019, and entitled "HEART AND LUNG MONITORING WITH COHERENT SIGNAL DISPERSION," which is a National Phase of Patent Cooperation Treaty Appl. No. PCT/US2018/016927, filed Feb. 5, 2018, and entitled "HEART AND LUNG MONITORING WITH COHERENT SIGNAL DISPERSION," which (i) claims priority to U.S. Ser. No. 62/454,437, filed Feb. 3, 2017, and entitled "HEART AND LUNG MONITORING WITH COHERENT SIGNAL DISPERSION"; and (ii) is a continuation-in-part of U.S. Ser. No. 14/936,536, filed Nov. 9, 2015, and entitled "COHERENT SIGNAL ANALYZER." Each of the applications for which a foreign or domestic priority claim is identified in the Application Data Sheet as filed with the present application is hereby incorporated by reference in its entirety under 37 CFR 1.57.

BACKGROUND

Field

This disclosure relates generally to systems and methods for analyzing signals that have propagated from a transmitter to a receiver through a channel as waves in order to obtain information about the transmitter, the receiver, and/or the channel (including a target located in the channel). More particularly, this disclosure relates to systems and methods for sensing heart and/or lung activity for a patient or other subject by performing coherent signal synthesis (at the transmitter) and/or analysis (at the receiver) to obtain information about the transmitter, receiver, and/or a frequency-selective channel, such as a multipath channel.

Description of the Related Art

Traditional heart and lung monitoring devices measure physiological activity using various technologies, but they typically require direct contact with the patient. A stethoscope amplifies sound waves from a beating heart or breathing lungs. An electrocardiograph (ECG) monitors the heart's electric field as transmitted to the skin. Echocardiography assesses cardiac wall and valvular motion via ultrasound reflections. Lung monitoring may be done via a ventilator which measures breath inhalation/exhalation through a face-worn mask and tube.

However, making direct contact with a patient could be undesirable, difficult, problematic, or even impossible in certain situations. For example, combat medics have to treat and evaluate casualties on the battlefield and evacuate them to a battalion aid station (BAS) under difficult conditions which may make contact-based monitors difficult to use. And a badly wounded person, such as a soldier in triage, may not easily be monitored with contact-based monitors. Alzheimer patients may tear off contact-based monitors. Veterans with post-traumatic stress disorder (PTSD) on average exhibit increased chronic cardiovascular arousal, including elevated heart rates in their sleep, but it is difficult for patients to wear contact-based monitors while sleeping. A homecare patient may forget to "wear" a monitor. A contact-based neonatal or fetal heart rate monitor may not remain secured to enable monitoring. A downed soldier or miner might exhibit signs of life but might not be accessible to a contact-based monitor. These cases, and others, could benefit from a monitoring solution that employs remote sensing technology, such as one which uses electromagnetic radiation (e.g., radio frequency (RF) waves).

The propagation of electromagnetic waves, such as RF waves, and their behavior when interacting with the world around us has long been studied. A practical application of this field of study has involved transmitting waves toward a target and then detecting those waves after their interaction with the target as a means to learn information about the target. Many systems and techniques have been developed for this purpose. Nevertheless, there remains a need for new systems and techniques for using transmitted and received signals to gain information about a transmitter, receiver, and/or propagation channel (including a target, such as a medical patient, located in the channel).

SUMMARY

In some embodiments, a method for sensing a physiological characteristic of a subject comprises: providing at least one receiver antenna in proximity to a portion of the subject's body; obtaining at least one receiver signal resulting from at least one transmitter signal that has propagated to the receiver antenna and has been reflected, diffracted, scattered, or transmitted by or through the portion of the subject's body; forming at least a first signal pair which comprises a first receiver signal and a first transmitter signal, or first and second receiver signals which are obtained from spatially-separated receiver antennas, or first and second receiver signals which are attributable to different transmitter signals, or first and second receiver signals which are obtained from non-orthogonally polarized portions of one or more receiver antennas, or a beam associated with a plurality of receiver antennas or a beam associated with a plurality of transmitter antennas, or a combination transmitter signal comprising a combination of two or more transmitter signals or a combination receiver signal comprising a combination of two or more receiver signals; determining amplitude and phase information of a plurality of frequency components for each signal in the first signal pair; and determining a set of comparison values for the first signal pair by comparing respective frequency component phases and respective frequency component amplitudes of the signals in the first signal pair.

In some embodiments, a system for monitoring a physiological characteristic of a subject comprises: at least one receiver antenna; and a processor configured to obtain at least one receiver signal resulting from at least one transmitter signal that has propagated to the receiver antenna and has been reflected, diffracted, scattered, or transmitted by or through at least a portion of the subject's body; form at least a first signal pair which comprises a first receiver signal and a first transmitter signal, or first and second receiver signals which are obtained from spatially-separated receiver antennas, or first and second receiver signals which are attributable to different transmitter signals, or first and second receiver signals which are obtained from non-orthogonally polarized portions of one or more receiver antennas, or a coherent beam signal associated with a plurality of receiver antennas or a coherent beam signal associated with a plurality of transmitter antennas, or a combination transmitter signal comprising a combination of two or more transmitter signals or a combination receiver signal comprising a combination of two or more receiver signals; determine amplitude and phase information of a plurality of frequency components for each signal in the first signal pair; and determine a set of comparison values for the first signal pair by comparing respective frequency component phases and respective frequency component amplitudes of the signals in the first signal pair.

BRIEF DESCRIPTION OF THE DRAWINGS

FIG. 3B is a table which lists the signal pairs whose frequency component phases and/or amplitudes can be compared to determine coherent signal dispersion information for the system shown in FIG. 3A.

FIG. 4B is a table which lists the signal pairs whose frequency component phases and/or amplitudes can be compared to determine coherent signal dispersion information for the system shown in FIG. 4A.

FIG. 5D is a table which lists the signal pairs whose frequency component phases and/or amplitudes can be compared to determine coherent signal dispersion information for the system shown in FIG. 5A.

DETAILED DESCRIPTION

The systems and methods described herein are useful for analyzing signals that have propagated from a transmitter to a receiver through a frequency-selective channel, such as a multipath channel, in order to determine information about the transmitter, the receiver, and/or the channel (including one or more targets located in the channel). As discussed further herein, the channel can include a medical patient's body, such as, for example, the thorax of the patient's body. The systems and methods described herein can be used to detect heart and lung functions, among other possible physiological processes. These systems and methods can take advantage of, for example, multipath propagation effects that cause modified versions of a transmitted signal to arrive at the receiver after having traversed the multipath channel. (Such multipath propagation effects are discussed with respect to FIG. 1.) These modified versions of the transmitted signals which are detected at the receiver can be compared with one another and/or with the original transmitted signals themselves in order to determine information about the transmitter, the receiver, and/or the channel.

Figure 1:
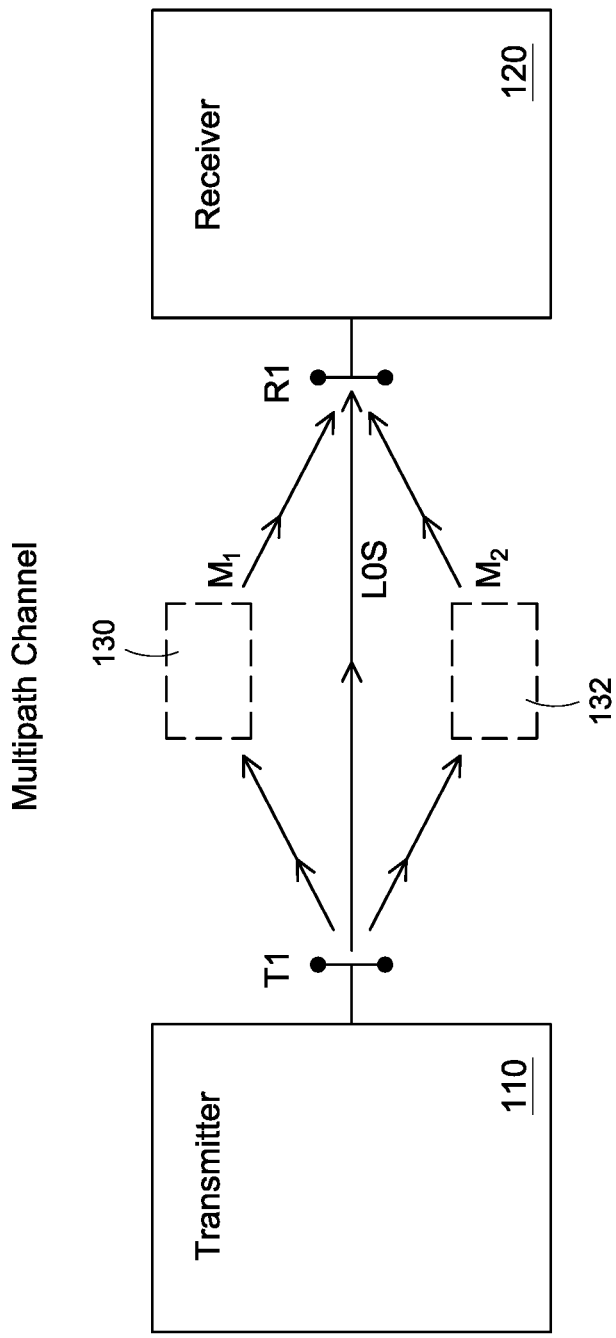
FIG. 1 illustrates a radio frequency (RF) transmitter and receiver operating in a multipath channel.

FIG. 1 illustrates a radio frequency (RF) transmitter 110 and receiver 120 operating in a multipath channel. The transmitter 110 includes an antenna T1 which transmits RF waves into the multipath channel. The RF waves are received by the receiver antenna R1. The multipath channel includes one or more targets 130, 132 which reflect, refract, diffract, scatter, or otherwise cause the transmitted radio waves to arrive at the receiver antenna R1 along multiple paths.

In the illustrated example, RF waves from the transmitter antenna T1 arrive at the receiver antenna R1 along a line of sight (LOS) pathway and two other multipaths $M_1$ and $M_2$ which result from the presence of the targets 130, 132. In some cases, the multipath effects introduced by the targets 130, 132 can be time-varying. For example, a target in the multipath channel can be physically moving or it can have some other time-varying characteristic which affects the RF waves received at the receiver. The collective response consisting of effects from the transmitter, the channel, and the receiver can be referred to as the system response, the system impulse response, the system transfer function, the time varying system impulse response, the time-varying system transfer function, etc.

In many applications, multipath signals are undesirable and are often considered to be an impairment. However, the systems and methods described herein can take advantage of multipath propagation effects (or other effects which occur in other types of frequency-selective channels) to detect changes in the propagation channel, including changes in one or more characteristics of the targets 130, 132. Multipath propagation effects can modify a transmitted signal in many ways, including by introducing (through scattering, reflection, refraction, diffraction, etc.) constructive or destructive interference, phase shifting, time delay, frequency shifting, and/or polarization changes to each multipath component. The systems and methods described herein can use techniques for identifying, measuring, and/or otherwise analyzing any of these effects, or others, to gain information about the multipath channel, including the targets 130, 132 located in the channel. It should be understood, however, that while various embodiments in this application are described in the context of multipath propagation channels, the systems and techniques described herein are also applicable to other types of frequency-selective channels. For example, the channel could be one in which one (or perhaps more) path(s) are themselves frequency-selective, such as a frequency-selective medium or a frequency selective surface reflection.

In addition, besides being used to gain information about the channel (including one or more targets located in the channel), the systems and methods described herein can also be used to gain information about the transmitter and/or the receiver. For example, the systems and methods discussed herein can be used to identify or characterize changes in the polarization state of the transmitted signals, changes in the orientation or location of transmitter antennas, changes in a combination of signals from multiple transmitter antennas (e.g., changes in the amplitude and/or phase weighting factors applied to multiple transmitted signals), changes in the relative delays between transmitted signals, etc. Similarly, the systems and methods discussed herein can be used to identify or characterize similar effects at the receiver. Any of these effects impacting the system response can be identified, measured, and/or otherwise analyzed to gain information about the transmitter, the receiver, and/or the channel (including the targets 130, 132 located in the channel).

Thus, the systems and methods described herein can characterize not only the channel but also the transmitter and/or receiver. For example, if the transmitter and receiver are fixed, then the measured signals can be used to characterize changes in the channel. But for a fixed channel and a fixed receiver, the measured signals can characterize changes in the location and/or properties of the transmitter. Similarly, for a fixed transmitter and channel, the received signals can characterize changes in the location and/or properties of the receiver. Or, in general, the measured signals can contain information about transmitter effects, channel effects, and receiver effects (which effects may or may not be separable).

The received signal(s) represent the convolution of the transmitted signal(s) with the channel, and hence is/are a function of the transmitted signal. When the transmitted signal(s) is/are known, that knowledge can be used by the receiver to estimate the system response, typically with greater accuracy than if the transmitter signal is not known. This capability has an advantage of limiting the impacts due to the specific waveforms that are transmitted, especially those exhibiting any time-varying spectral properties.

Figure 2:
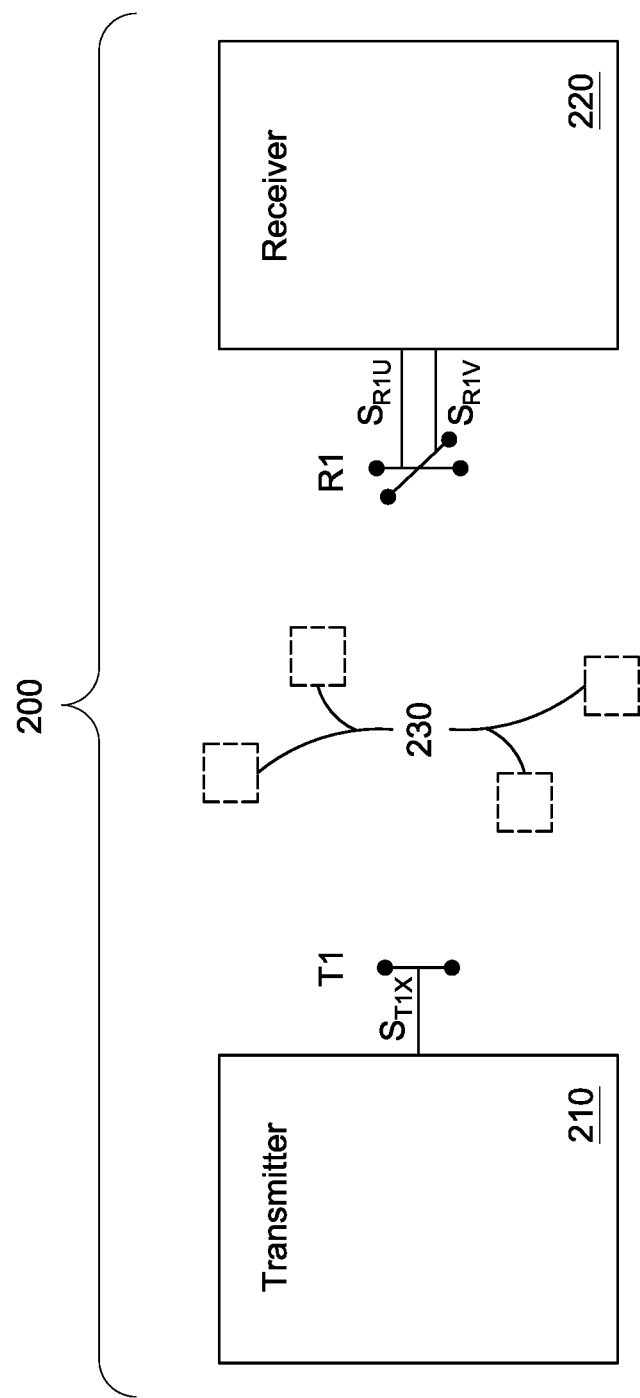
FIG. 2 illustrates a system for characterizing polarization mode dispersion in signals measured at a receiver after propagating through a channel, such as a multipath channel.

FIG. 2 illustrates a system 200 for characterizing polarization mode dispersion in signals measured at a receiver after propagating through a channel, such as a multipath channel. The phenomenon referred to herein as polarization mode dispersion can generally be understood as a variation in the polarization state of the received signal as a function of the signal's frequency components (i.e., the polarization state(s) is/are altered distinctly for the different frequency components of the received signal(s)). Polarization mode dispersion can occur, for example, in channels exhibiting both a delay spread between signals carried by orthogonally-polarized waves and power coupling between the polarization modes. One example of polarization mode dispersion is that the channel may couple vertically polarized waves into horizontally polarized waves on paths with different delays relative to the vertically polarized path, possibly in a frequency-dependent fashion, or vice versa. For each polarization mode, the complex transfer function gains (amplitude and phase) in the channel may exhibit distinct variations as a function of frequency, leading to polarization mode dispersion. The polarization mode dispersion can be introduced by the transmitter, the channel, or the receiver. For example, polarization mode dispersion can be caused by a frequency-selective channel, such as a multipath channel, or by intentionally-introduced polarization mode dispersion at the transmitter, or can be introduced at the receiver by using received signals that are delayed relative to each other.

The system 200 illustrated in FIG. 2 includes a transmitter 210 with a polarized transmitting antenna T1. The antenna T1 has x-polarization, which could arbitrarily be vertical, horizontal, right or left-hand circular, slant±45°, etc. The system 200 also includes a receiver 220 with a dual polarized receiving antenna R1. The dual polarized receiving antenna R1 is u-polarized and v-polarized, where u and v represent any pair of orthogonal polarizations, including vertical and horizontal, right and left-hand circular, slant+ 45° and slant−45°, etc. In some embodiments, either the u- or v-polarization is co-polarized with the x-polarization of the transmitting antenna T1, but this is not required.

The transmitter 210 transmits a signal $S_{T1x}$ of bandwidth BW centered at RF frequency $f_0$. One way to accomplish this is to generate a baseband signal of bandwidth BW and to up-convert this signal to an RF carrier frequency $f_0$. The resulting signal may be transmitted through the transmitter antenna T1. Alternatively, the transmitter can transmit a signal consisting of at least two tones that are spaced apart in frequency, or the transmitter can sweep the frequency of a tone or pulse an RF tone. In some embodiments, a signal having a bandwidth BW centered at the RF frequency $f_0$ can be directly generated using digital signal processing followed by digital-to-analog conversion. Other methods of signal generation are also possible.

The transmitted signal emitted from the transmitter antenna T1 begins propagating through the multipath channel as x-polarized RF waves across the full range of frequencies comprising the bandwidth BW of the transmitted signal. In the case considered, the multipath channel includes one or more targets 230 which introduce multipath contributions at the receiver 220, which can result in a frequency-selective vector propagation channel (i.e., a frequency-selective channel for at least one of the polarization modes) if path delays among the components exhibit sufficient spread. The receiving antenna R1 detects orthogonally-polarized channel-modified versions of the transmitted RF signal. The signal $S_{R1u}$ represents the u-polarized component of the detected signal, whereas the signal $S_{R1v}$ represents the v-polarized component. These orthogonally-polarized signals can be processed at the receiver 220 in order to determine information about the transmitter, the channel, and/or the receiver. If the transmitter and receiver are fixed, for example, then the received signals can be used to detect and characterize changes in the multipath channel. This is discussed in U.S. Patent Publication 2013/0332115, the entire contents of which are hereby incorporated by reference in this disclosure.

In some embodiments, the receiver 220 down-converts the received RF signals and performs analog-to-digital conversion. The down-converted signals can be represented in any suitable form, including as in-phase and quadrature signal components. The down-converted $S_{R1u}$ and $S_{R1v}$ signals can be analyzed sub-band by sub-band. For example, the receiver 220 can perform an N-point fast Fourier transform (FFT), or other suitable transform, to convert the signals into N bins in the frequency domain. Each of these frequency bins can be considered as a sub-band (also referred to as a sub-frequency or sub-carrier). If, for example, the originally-transmitted baseband signal has a bandwidth of 20 MHz, the received $S_{R1u}$ and $S_{R1v}$ signals can divide the 20 MHz bandwidth into any number of sub-bands which can then be considered independently, or in combination, to analyze the transmitter-channel-receiver system as a function of frequency.

In some embodiments, the receiver 220 calculates the polarization for each sub-band by using the frequency-domain representations of the baseband $S_{R1u}$ and $S_{R1v}$ signals to calculate a Jones vector or Stokes parameters (which can be obtained by calculating the Jones coherency matrix). These calculations are known in the art and examples are provided in U.S. Patent Publication 2013/0332115, which are incorporated herein by reference. When calculated using signals from a dual polarization (orthogonally-polarized) antenna, the result of these computations is polarization state information. The polarization information may be computed for each sub-band of the down-converted baseband signals received at the antenna R1. The polarization can be measured in a relative sense, or, if the orientation of the receiver antenna R1 is known, in an absolute sense. Polarization statistics, such as the degree of polarization can also be measured for the entire signal. Alternatively, repeated measurements of the state of polarization for each sub-band can be used to characterize the degree of polarization associated with the sub-band.

The polarization state information characterizes the polarization mode dispersion—the frequency-dependency of the polarization mode shifting—caused by the channel or other factors. The polarization values (e.g., the Stokes parameters) for each sub-band can be normalized, where the $S_1$, $S_2$, and $S_3$ Stokes parameters are scaled to form a vector of unit magnitude, depending upon whether or not the signal has a unity degree of polarization. (Using a small enough sub-band spacing will generally yield a degree of polarization near unity in each sub-band.) The resulting polarization values may be plotted on or about a Poincaré sphere as a visualization aid. For example, the normalized $S_1$, $S_2$, and $S_3$ Stokes parameters for each sub-band can be taken as coordinates and plotted on the Poincaré sphere (which has a unit radius) as a point. Each location on the Poincaré sphere corresponds to a different polarization state. When the Stokes parameters for multiple sub-bands are plotted, the result is a locus of points which can be referred to as a polarization mode dispersion (PMD) curve. As discussed in U.S. Patent Publication 2013/0332115, PMD curves can be analyzed to determine information about the multipath channel. They may also provide information about any other type of frequency selective channel or about any portion of the transmitter-channel-receiver system.

While normalization of the $S_1$, $S_2$, and $S_3$ Stokes parameters to a unit vector may be advantageous in some embodiments, in other embodiments retaining the amplitude information in the parameters is desirable, in which case the $S_0$ value will be maintained along with $S_1$, $S_2$, $S_3$. The unnormalized parameters $S_1$, $S_2$, and $S_3$ taken from the full Stokes vector $[S_0\ S_1\ S_2\ S_3]$ can also be plotted in 3D space, but will not, in general, be confined to a locus that resides on a unit sphere, yet the resulting curve may still be analyzed to determine information about the transmitter-channel-receiver system. Also, it may also be useful to retain RF phase information of the signals used in the formation of the Stokes parameters.

Figure 4A:
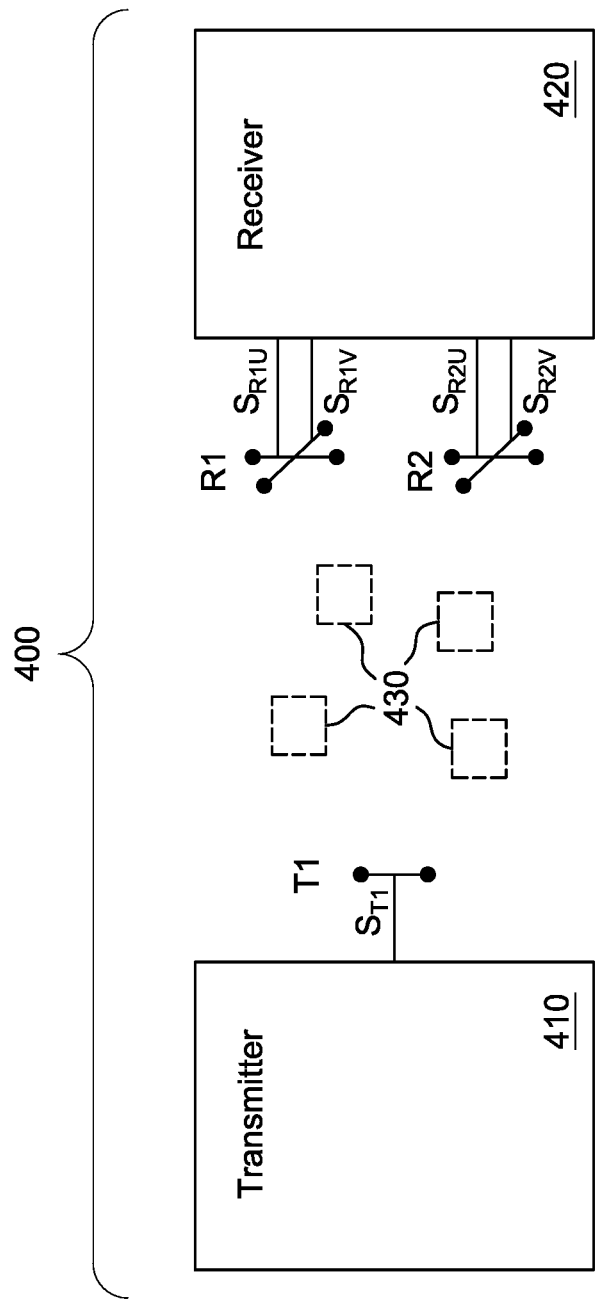
FIG. 4A illustrates a system for analyzing a transmitter-channel-receiver system using one transmitting antenna and two spatially-separated, dual polarized receiving antennas.
Figure 5A:
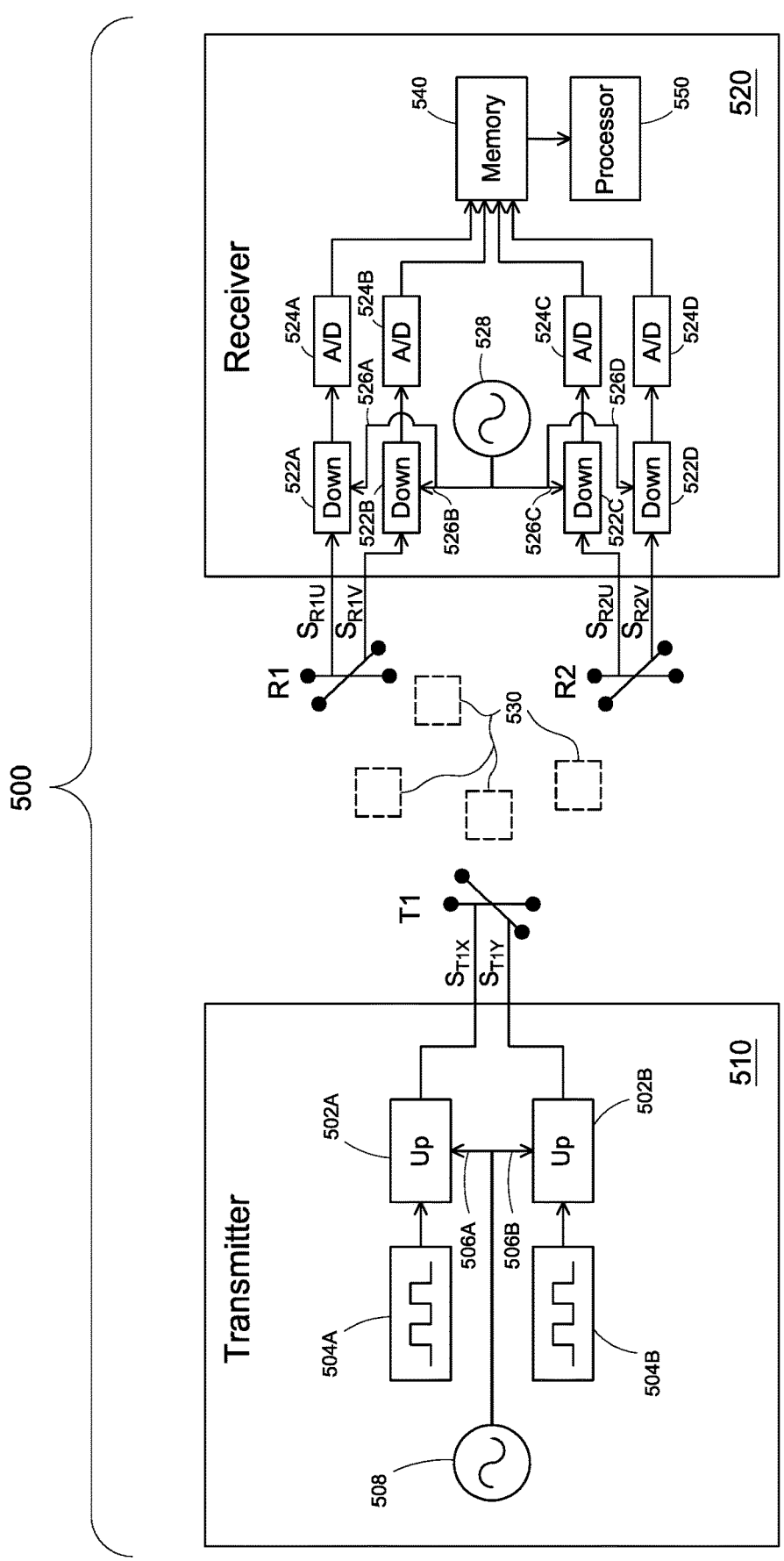
FIG. 5A illustrates a system for analyzing a transmitter-channel-receiver system using one dual polarized transmitting antenna and two spatially-separated, dual polarized receiving antennas.

While FIG. 2 illustrates a system for analyzing polarization mode dispersion, other system architectures and methods can be used to analyze effects from the transmitter-channel-receiver system. These other system architectures and methods can yield valuable additional information about any portion of the transmitter-channel-receiver system. Examples of these other system architectures are illustrated in FIGS. 3A, 4A, and 5A.

Figure 3A:
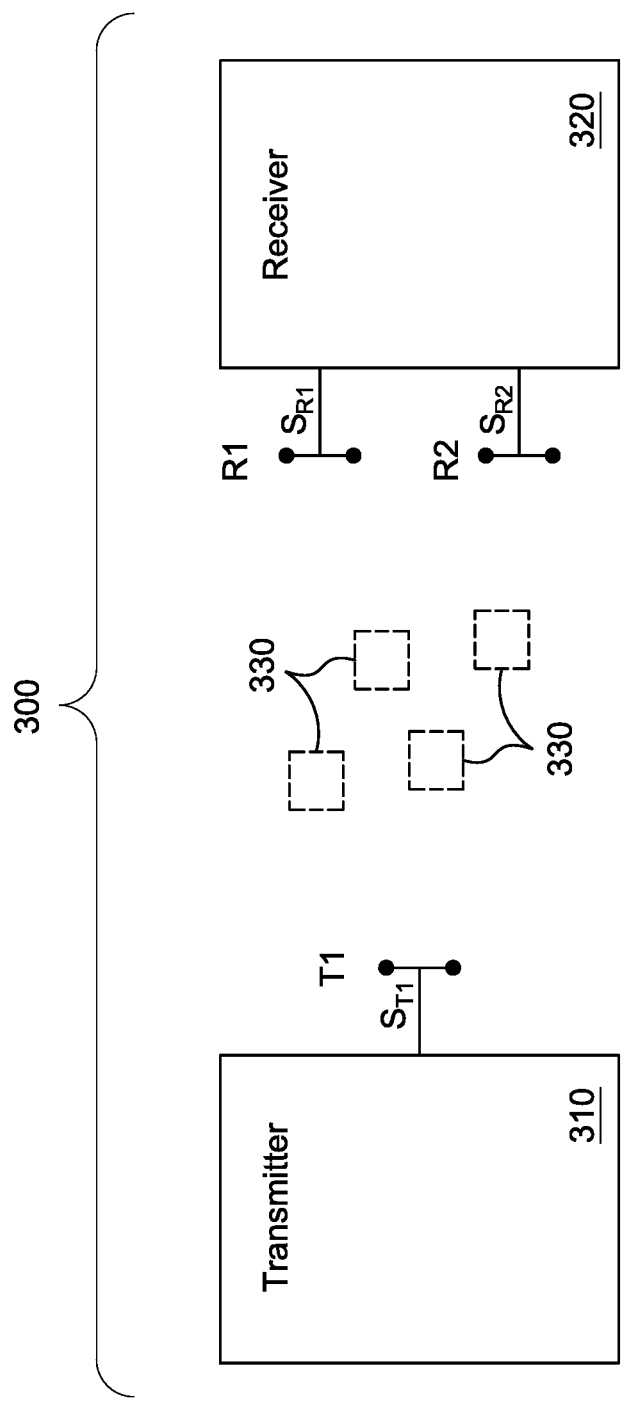
FIG. 3A illustrates a system for analyzing a transmitter-channel-receiver system using one transmitting antenna and two spatially-separated receiving antennas.

FIG. 3A illustrates a system 300 for analyzing a transmitter-channel-receiver system using one transmitting antenna and two spatially-separated receiving antennas. The system 300 includes a transmitter 310 with a transmitting antenna T1. The transmitting antenna T1 can be arbitrarily polarized. The system 300 also includes a receiver 320 with two spatially-separated receiving antennas R1, R2. In some embodiments, the receiving antennas R1, R2 are typically separated by at least 0.5 wavelengths of the RF carrier frequency used by the transmitter 310. The receiving antennas R1, R2 can each have arbitrary polarization(s) that need not be the same as each other or the same as the polarization of the transmitting antenna T1.

The transmitter 310 transmits a signal $S_{T1}$ with a bandwidth BW centered at an RF frequency $f_0$ via the antenna T1. The transmitter signal can be generated in any way disclosed herein, for example. The signal propagates through a frequency-selective channel, such as a multipath channel, with one or more targets 330 that create a frequency-selective response at the receiving antennas R1, R2. The channel, for example, can cause different modified versions of the transmitted signal $S_{T1}$ to be received at the spatially-separated receiving antennas R1, R2. The signal $S_{R1}$ represents the signal received at R1, whereas the signal $S_{R2}$ represents the signal received at R2. The receiver 320 can down-convert these signals and perform analog-to-digital conversion. As discussed further herein, the received signals $S_{R1}$ and $S_{R2}$ can be coherently received (e.g., coherently sampled and processed). In addition, the two receiver channels for these signals can be phase and/or gain matched.

Once, the $S_{R1}$ and $S_{R2}$ signals are down-converted and sampled, the frequency component phases and amplitudes of the baseband $S_{R1}$ and $S_{R2}$ signals can be compared. This can be done in the time domain (e.g., via a filter bank) or in the frequency domain. For example, each of the received signals can be converted into the frequency domain using an N-point FFT operation. This operation divides the bandwidth of each of the down-converted $S_{R1}$ and $S_{R2}$ signals into N frequency bins. The respective amplitudes and phases of the frequency components of the $S_{R1}$ and $S_{R2}$ signals can then be compared for each sub-band. For example, the amplitudes of the frequency components of one of the signals can be compared to those of the other by calculating differences between the respective amplitudes or ratios of the amplitudes. Similarly, the phases of the frequency components of one of the signals can be compared to those of the other by calculating differences between the respective phases. These are just some examples of computations which can be performed to compare the respective amplitudes and/or phases. Many others are also possible. For example, in some embodiments, the respective amplitudes and phases of the frequency components of the $S_{R1}$ and $S_{R2}$ signals can be compared by calculating a Jones vector or Stokes parameters (normalized or unnormalized) for each sub-band using the $S_{R1}/S_{R2}$ signal pair. Other mathematical computations can also be used to compare the phases and/or amplitudes of the frequency components of the two signals.

If the $S_{R1}$ and $S_{R2}$ signals had been obtained from a dual polarized antenna, then the results of this computation would be polarization information (as already discussed above with respect to FIG. 2). However, because the receiving antennas R1 and R2 are not substantially co-located, nor do they necessarily sample orthogonally-polarized components of the transmitted signal, the result of the Jones vector or Stokes parameter computation does not quantify polarization. In fact, the resulting values do not describe any particular known physical quantity. Nevertheless, the comparison of the respective amplitude and/or phase of the signals received at spatially-separated antennas, for each frequency sub-band, can still provide useful information about the transmitter-channel-receiver system. While the resulting values are not polarization values, they can still be plotted for each sub-band on or about a unit sphere (similar to a Poincaré sphere) as a visualization aid. (If normalization is applied, the signals will fall on a unit sphere, otherwise, in general they will not be confined to a unit sphere.) The resulting locus of points is not a polarization mode dispersion (PMD) curve, however. Instead, the resulting curve can be referred to as a coherent signal dispersion curve (CSDC). Furthermore, besides the received signals being compared with one another, the amplitudes and/or phases of the frequency components of the received signals $S_{R1}$ and $S_{R2}$ can also be compared with those of the original transmitted signal $S_{T1}$. Again, this comparison of the amplitudes and/or phases of the frequency components of the received signals with those of the original transmitted signal can be done on a per sub-band basis.

Figure 3B:
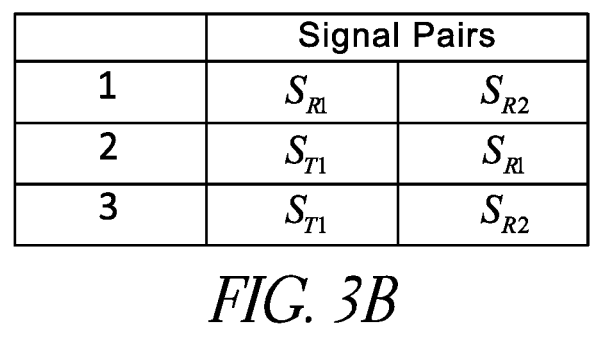

FIG. 3B is a table which lists the signal pairs whose frequency component phases and/or amplitudes can be compared to determine coherent signal dispersion information for the system 300 shown in FIG. 3A. As already discussed, the system 300 in FIG. 3A includes one transmitter channel and two receiver channels that are obtained from spatially-separated antennas. As shown in the table of FIG. 3B, the system provides three signal pairs whose respective frequency component phases and/or amplitudes can be compared in order to determine information about the transmitter-channel-receiver system. Namely, the respective frequency component phases and/or amplitudes of the two received signals $S_{R1}$ and $S_{R2}$ can be compared with one another. This is the first signal pair shown in the table in FIG. 3B. In addition, the respective frequency component phases and/or amplitudes of these two received signals $S_{R1}$ and $S_{R2}$ can also each be compared with those of the original transmitted signal $S_{T1}$. These are the second and third signal pairs shown in the table in FIG. 3B. The system 300 illustrated in FIG. 3A can therefore provide three coherent signal dispersion curves. Each of these curves can be analyzed, as discussed herein, to determine information about the transmitter, receiver, and/or channel (including characteristics of one or more objects in the channel).

As just mentioned, the respective frequency component amplitudes and/or phases of each of these signal pairs can be compared (e.g., for each sub-band). (As already disclosed, one example of the comparison values that can be calculated are the Stokes parameters for each sub-band of each signal pair. Stokes parameters ($S_0$, $S_1$, $S_2$, and $S_3$) for each sub-band can be calculated according to the following equations: $S_0=(Y_1 \cdot Y_1^*)+(Y_2 \cdot Y_2^*)$; $S_1=(Y_1 \cdot Y_1^*)-(Y_2 \cdot Y_2^*)$; $S_2=(Y_1 \cdot Y_2^*)+(Y_2 \cdot Y_1^*)$; and $S_3=j(Y_1 \cdot Y_2^*)-j(Y_2 \cdot Y_1^*)$, where $Y_1$ is a complex number with amplitude and/or phase information for a first signal in the pair of signals being compared and $Y_2$ is a complex number with amplitude and/or phase information for a second signal in the pair of signals being compared.) The phases can be measured only in a relative sense with respect to one another or with respect to a local oscillator at the receiver 320. Alternatively, and/or additionally, the phases can be measured with respect to a phase reference (e.g., a local oscillator) at the transmitter 310. Frequency dispersion statistics (likened to degree of polarization) can be determined for each sub-band. Other computations for estimating the same or similar information can be calculated from power measurements as described in Pratt et al., "A Modified XPC Characterization for Polarimetric Channels," IEEE Transactions on Vehicular Technology, Vol. 60, No. 7, September 2011, p. 20904-2013. This reference describes polarization characterizations, but the same techniques can be applied to the signals pairs disclosed herein even though they will not result in polarization information. This reference is therefore incorporated by reference herein in its entirety for its disclosure of such analysis techniques.

In some embodiments, the receiver 320 can include more than two receiving antennas to obtain additional receiver signals. In addition, in some embodiments, the system 300 architecture can be reversed from what is shown and can instead include two or more transmitter antennas for sending two or more transmitter signals and only one receiver antenna for obtaining a receiver signal. (In embodiments with two or more transmitter signals, the transmitter signals can be coherently synthesized, as discussed further herein.) Or the system 300 could include two or more transmitter antennas (for sending two or more transmitter signals) and two or more receiver antennas (for obtaining two or more receiver signals). In any case, all of the resulting signal pairs can be used to analyze the system, as disclosed herein.

FIG. 4A illustrates a system 400 for analyzing a transmitter-channel-receiver system using one transmitting antenna and two spatially-separated dual polarized receiving antennas. The system 400 includes a transmitter 410 with a transmitting antenna T1. The transmitting antenna T1 can be arbitrarily polarized. The system 400 also includes a receiver 420 with two spatially-separated receiving antennas R1, R2. In some embodiments, the receiving antennas R1, R2 are typically separated by at least 0.5 wavelengths of the RF carrier frequency used by the transmitter 410. The receiving antennas R1, R2 are both dual polarized. The dual polarized receiving antenna R1 is u-polarized and v-polarized, where u and v represent any pair of orthogonal polarizations, including vertical and horizontal, right and left-hand circular, slant+450 and slant−45°, etc. In some embodiments, either the u- or v-polarization is co-polarized with the polarization of the transmitting antenna T1, but this is not required. In some embodiments, the second dual polarized receiving antenna R2 is also u-polarized and v-polarized. However, in other embodiments, the orthogonal polarizations of the second receiving antenna R2 can be different than those of the first receiving antenna R1.

The transmitter 410 transmits a signal $S_{T1}$ with a bandwidth BW centered at an RF carrier frequency $f_0$ via the antenna T1. The signal $S_{T1}$ can be generated using any technique disclosed herein or any other suitable technique. The channel can include one or more targets 430 which create one or more signal paths to the receiving antennas R1, R2. These signal paths result in frequency-selective propagation effects that typically cause different modified versions of the transmitted signal $S_{T1}$ to be received at the spatially-separated dual polarized receiving antennas R1, R2. The first receiving antenna R1 detects orthogonally-polarized components of channel-modified versions of the transmitted RF signal. The signal $S_{R1u}$ represents the u-polarized component of the detected signal at the first receiving antenna R1, whereas the signal $S_{R1v}$ represents the v-polarized component. The second receiving antenna R2 likewise detects orthogonally-polarized components of channel-modified versions of the transmitted RF signal. The signal $S_{R2u}$ represents the u-polarized component of the detected signal at the second receiving antenna R2, whereas the signal $S_{R2v}$ represents the v-polarized component.

The orthogonally-polarized signal components from each of the receiving antennas R1, R2 can be processed at the receiver 420 in order to determine information about the transmitter-channel-receiver system. The receiver 420 can down-convert these signals and perform analog-to-digital conversion. As discussed further herein, the received signals $S_{R1u}$, $S_{R1v}$, $S_{R2u}$, and $S_{R2v}$ can be coherently received (e.g., coherently sampled and processed). In addition, the four receiver channels for these signals can be phase and/or gain matched. Once, the $S_{R1u}$, $S_{R1v}$, $S_{R2u}$, and $S_{R2v}$ signals are down-converted and sampled, the frequency component phases and amplitudes of various signal pairs can be compared. The different signal pairs are described below with respect to FIG. 4B. Additionally, the absolute frequency component phases and amplitudes for each signal pair can be measured (relative to some reference) and signal statistics such as those comparable to degree of polarization can also be computed.

Each of the received signals $S_{R1u}$, $S_{R1v}$, $S_{R2u}$, and $S_{R2v}$ can be converted into the frequency domain using an N-point FFT operation. This operation divides the bandwidth of each of the baseband $S_{R1u}$, $S_{R1v}$, $S_{R2u}$, and $S_{R2v}$ signals into N frequency bins. The respective frequency component amplitudes and phases of the various pairs of signals can then be compared for each sub-band using any calculation discussed herein or any other suitable calculation. In some embodiments, the respective frequency component amplitudes and phases for a particular signal pair can be compared by, for example, calculating a Jones vector or Stokes parameters (normalized or unnormalized) for each sub-band. Additionally absolute phase and amplitude information and statistics can also be measured.

FIG. 4B is a table which lists the signal pairs whose frequency component phases and/or amplitudes can be compared to determine coherent signal dispersion information for the system 400 shown in FIG. 4A. As already discussed, the system 400 in FIG. 4A includes one transmitter channel and four receiver channels, which are obtained from spatially-separated, dual polarized antennas. As shown in the table of FIG. 4B, the system 400 provides 10 signal pairs whose respective frequency component phases and/or amplitudes can be compared in order to determine information about the transmitter-channel-receiver system. The first six signal pairs are formed by the various combinations of the received signals $S_{R1u}$, $S_{R1v}$, $S_{R2u}$, and $S_{R2v}$. The first signal pair is made up of the RF signals detected at the first antenna R1. These are $S_{R1u}$ and $S_{R1v}$. The second signal pair is made up of the RF signals detected at the second antenna R2. These are $S_{R2u}$ and $S_{R2v}$. In both of these cases, polarization information can be obtained by comparing the phases and/or amplitudes of the signals in each pair.

Additional information about the transmitter-channel-receiver system can be obtained by also comparing respective frequency component phases and/or amplitudes from signals detected at different antennas. A total of four signal pairs can be formed to make these "cross-antenna" comparisons. These are signal pairs 3-6 in the table shown in FIG. 4B. They consist of the two u-polarization signals, $S_{R1u}$ and $S_{R2u}$; the two v-polarization signals, $S_{R1v}$ and $S_{R2v}$; the u-polarization signal from the first antenna and the v-polarization signal from the second antenna, $S_{R1u}$ and $S_{R2v}$; and finally the v-polarization signal from the first antenna and the u-polarization signal from the second antenna, $S_{R1v}$ and $S_{R2u}$. The values which result from these cross-antenna comparisons of respective frequency component phases and/or amplitudes (i.e., the values calculated from signal pairs 3-6 in the table shown in FIG. 4B) are not polarization values. Nevertheless, they can include important information about the transmitter-channel-receiver system (including effects due to one or more objects within the channel).

The first six signal pairs in the table shown in FIG. 4B are made up of only the received signals. However, still additional information about the transmitter-channel-receiver system can be obtained by comparing each of the received signals $S_{R1u}$, $S_{R1v}$, $S_{R2u}$, and $S_{R2v}$ with the original transmitted signal $S_{T1}$. These are signal pairs 7-10 shown in the table in FIG. 4B.

As discussed herein, the respective frequency component phases and/or amplitudes for each of the signal pairs from the table shown in FIG. 4B can be compared in a variety of ways. For example, this can be done for each signal pair on a per sub-band basis by calculating a Jones vector or Stokes parameters for each sub-band (e.g., using the equations disclosed herein). While the majority of the resulting calculated values are not polarization values, they can still be plotted on or about a unit sphere similar to a Poincaré sphere as a visualization aid. Two of the resulting ten curves are polarization mode dispersion (PMD) curves (i.e., those obtained from signal pairs 1 and 2 in the table of FIG. 4B). The other eight curves can be described as coherent signal dispersion curves (CSDC) (i.e., those obtained from signal pairs 3-10 in the table of FIG. 4B). Each of these curves can be analyzed, as discussed herein, to determine information about the transmitter-channel-receiver system, including characteristics of one or more objects in the channel. Additionally, absolute phase and/or amplitude information and statistics for each signal pair can also be measured.

In some embodiments, the receiver 420 can include more than two dual polarized receiving antennas to obtain additional receiver signals. In addition, in some embodiments, the system 400 architecture can be reversed from what is shown and can instead include two or more transmitter antennas (which can be spatially-separated and/or dual polarized) for sending two or more transmitter signals and only one receiver antenna (which can be dual polarized) for obtaining a receiver signal. Or the system 400 could include two or more transmitter antennas (for sending two or more transmitter signals) and two or more receiver antennas (for obtaining two or more receiver signals). In any case, all of the resulting signal pairs can be used to analyze the system, as disclosed herein.

FIG. 5A illustrates a system 500 for analyzing a transmitter-channel-receiver system using one dual polarized transmitting antenna and two spatially-separated, dual polarized receiving antennas. The system 500 includes a transmitter 510 with a transmitting antenna T1 that is dual polarized. (Although the system 500 is illustrated with a single transmitting antenna, multiple spatially-separated transmitting antennas could also be used.) The dual polarized transmitting antenna T1 is x-polarized and y-polarized, where x and y represent any pair of orthogonal polarizations, including vertical and horizontal, right and left-hand circular, slant+45° and slant−45°, etc. The system 500 also includes a receiver 520 with two spatially-separated receiving antennas R1, R2. In some embodiments, the receiving antennas R1, R2 are typically separated by at least 0.5 wavelengths of the RF carrier frequency used by the transmitter 510. The two receiving antennas R1, R2 can be dual polarized. The first dual polarized receiving antenna R1 is u-polarized and v-polarized, where u and v represent any pair of orthogonal polarizations, including vertical and horizontal, right and left-hand circular, slant+45° and slant−45°, etc. In some embodiments, either the u- or v-polarization is co-polarized with the x- or y-polarization of the transmitting antenna T1, but this is not required. In some embodiments, the second dual polarized receiving antenna R2 is also u-polarized and v-polarized. However, in other embodiments, the orthogonal polarizations of the second receiving antenna R2 can be different than those of the first receiving antenna R1.

The transmitter 510 includes two waveform generators 504a, 504b that can respectively provide baseband waveforms $S_{T1x}$ and $S_{T1y}$ that are coherently synthesized and centered at a carrier frequency $f_0$ and transmitted via the transmitting antenna T1. The waveform generators 504a, 504b can provide any of the following waveforms: single tone continuous wave, wideband noise, band-limited noise, chirp, stepped frequency, multi-tone, pulses, pulsed chirps, orthogonal frequency division multiplexing (OFDM), binary phase shift keying (BPSK), linear FM on pulse (LFMOP), etc. It should be understood, however, that these are just example waveforms and that a wide variety of other waveforms can also be used, including any desired arbitrary waveform that may be suited to a given application. Each of the waveform generators 504a, 504b can operate independently and can provide different waveforms at any given time. In some embodiments, the transmitted signals can be scaled and/or phase-shifted versions of one another. For example, when using a dual-polarized transmit channel, controlling the relative phase and amplitude between the orthogonally-polarized channels leads to control over the transmitted polarization state. In other embodiments, it is also possible to generate time-delayed signals, each with a controlled relative scaling and/or shift between the orthogonally-polarized channels, for example to intentionally induce dispersion.

The baseband waveforms produced by the waveform generators 504a, 504b are provided to up-converters 502a, 502b to be centered at an RF carrier frequency $f_0$. The RF carrier frequency is provided by the local oscillator 508. The carrier frequency is fed from the local oscillator 508 to the up-converters 502a, 502b via signal lines 506a, 506b. In some embodiments, the signal lines 506a, 506b are matched signal lines so as to maintain the phase coherency of the carrier frequency at the up-converters 502a, 502b. As shown in FIG. 5A, a single local oscillator 508 can feed both up-converters 502a, 502b. Alternatively, different local oscillators can respectively feed the up-converters 502a, 502b. If different local oscillators are used, they are preferably synchronized in phase and frequency. In some embodiments, the transmitter 510 operates coherently such that the transmitted signals $S_{T1x}$ and $S_{T1y}$ are coherently synthesized. FIG. 5A illustrates one system for coherently synthesizing transmit signals, but others can also be used. For example, the transmitter 510 can transmit a signal consisting of two or more coherent continuous-wave or pulsed (or otherwise modulated) RF tones. Or two or more coherent signals can be directly generated using digital signal processing followed by digital-to-analog conversion. Other methods of coherent signal generation are also possible.

As just discussed, in some embodiments, the transmitted signals are coherent. Phase information can be preserved between the various transmitter signals. One way to achieve coherency between the transmitted signals is to share a common local oscillator 508 used in the up-conversion processing. A common local oscillator can be advantageous in a multichannel transmitter because any impairments in the local oscillator may affect all channels relatively equally, thus not substantially affecting relative channel-to-channel comparisons. In some instances, control over the local oscillator phase may be advantageous, for example to assure that the starting phase reference for each transmitted signal is substantially identical (or if not identical then known so that the phase difference between transmitted signals can be compensated). In some embodiments, the transmitter can advantageously achieve precise control of the phase, amplitude, sampling, and frequency among the various generated signals used at the transmitter. Further, in some embodiments, the phase noise of the local oscillator 508 is negligible such that energy of a desired signal in one sub-band coupling to an adjacent sub-band is significantly less (e.g., two or more orders of magnitude less) than the signal being detected in that adjacent band.

In addition, in some embodiments, each signal channel in the transmitter can be substantially phase and gain matched with the others. In order to achieve this matching, compensation circuits can be included. For example, if the transmitter includes different amplifier circuits in each channel, then depending upon the transmit signal and the non-linear behavior of the amplifier in each channel, it may be possible for asymmetrical signal distortion to occur (e.g., the effects on one channel are not identical to the other channels). Such behavior could be detrimental to a coherent, matched system, and so compensation circuits can be used to reduce or minimize phase and gain mismatches in the channels.

Although the transmitter 510 in FIG. 5A is shown in more detail than the transmitters in preceding figures, each of the transmitters discussed herein can include elements and features similar to those discussed with respect to the transmitter 510 to coherently synthesize transmit signals.

In some embodiments, the transmitted signals $S_{T1x}$ and $S_{T1y}$ are advantageously separable. This means that the transmitted signals $S_{T1x}$ and $S_{T1y}$ have the property that they can be distinguished from one another by the receiver 520. For example, the different signals generated at the transmitter may be approximately orthogonal in some sense so that the signals can be separated at the receiver with little crosstalk among the signals. The multiple signals generated at the transmitter can be sent using a different signal on each antenna, or by using different linear combinations of multiple antennas to transmit each signal. In addition, the transmitted signals can employ, for example, a cyclic prefix to help reduce inter-symbol interference (non-orthogonal subcarriers).

The separability property of the transmitted signals can be achieved in several different ways, including, for example, through the use of time division multiplexing, frequency division multiplexing, and/or code division multiplexing. Methods based on eigendecomposition or singular value decomposition can also be used. Other methods may also be possible. In the case of time division multiplexing, the signals $S_{T1x}$ and $S_{T1y}$ can be transmitted during different time slots such that the receiver can distinguish the response of each of the receiving antennas to each of the transmitted signals. However, in many cases the system 500 is used to detect a time-varying property of a multipath channel. Therefore, it may be desirable to transmit both of the signals $S_{T1x}$ and $S_{T1y}$ at the same or overlapping times in order to more completely characterize the time-varying property. This is particularly true if the variations being monitored occur on a timescale that is short as compared to the length of the time slots for the transmitted signals. In cases where it is desirable that the signals $S_{T1x}$ and $S_{T1y}$ be transmitted at the same time (or at time periods which overlap), then frequency division multiplexing, code division multiplexing, eigendecomposition, singular value decomposition, and/or other methods can be used.

Figure 5B:
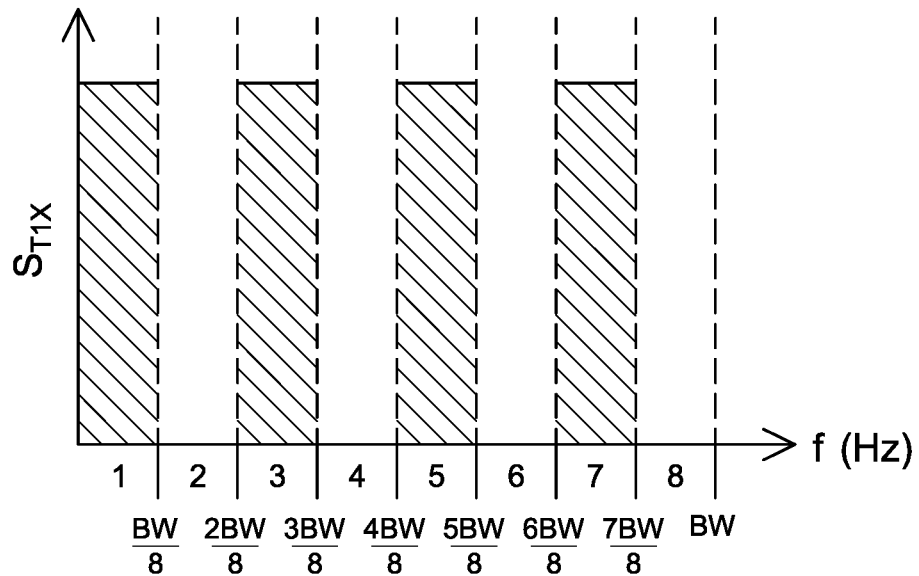
FIGS. 5B and 5C illustrate two separable transmitter signals which can be used in the system shown in FIG. 5A.
Figure 5C:
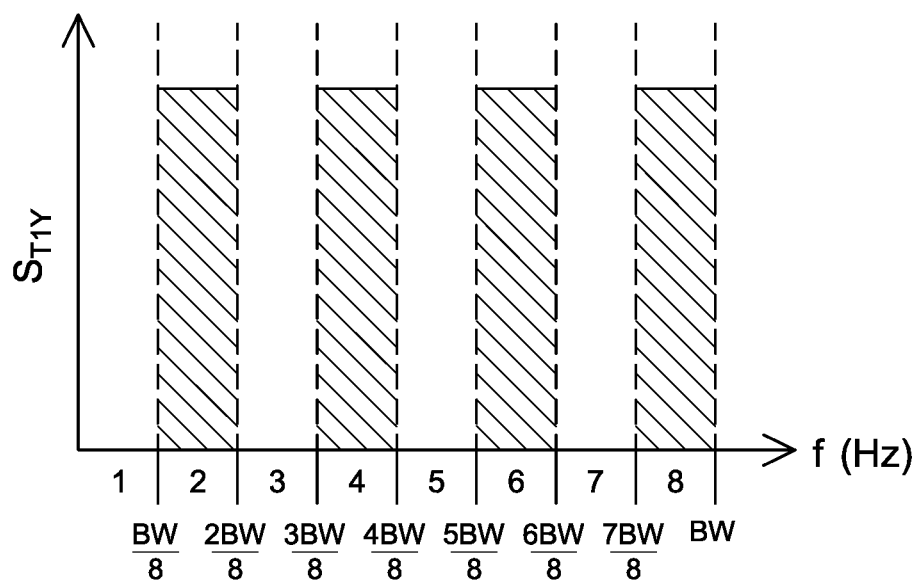

FIGS. 5B and 5C illustrate two separable transmitted signals which can be used in the system shown in FIG. 5A. In the illustrated example, the two transmitted signals are separable based on frequency division multiplexing. FIG. 5B shows an abstract representation of the transmitted signal $S_{T1x}$ in the frequency domain. The bandwidth (BW) of the signal $S_{T1x}$ is shown as being separated into 8 segments. The shaded regions indicate the frequency bands utilized by $S_{T1x}$. In this case, $S_{T1x}$ utilizes the odd frequency sub-bands (i.e., frequency sub-bands 1, 3, 5, and 7). Meanwhile, FIG. 5C shows an abstract representation of the transmitted signal $S_{T1y}$ in the frequency domain. Once again, the bandwidth (BW) of the signal $S_{T1y}$ is shown as being separated into eight segments and the shaded regions indicate the frequency sub-bands utilized by $S_{T1y}$. In this case, $S_{T1y}$ utilizes the even frequency sub-bands (i.e., frequency sub-bands 2, 4, 6, and 8). Because the signals $S_{T1x}$ and $S_{T1y}$ do not overlap in frequency, the response to each of these transmitted signals at the receiving antennas can be separately determined despite the fact that the signals may be transmitted at the same time. This separability property of the transmitted signals $S_{T1x}$ and $S_{T1y}$ allows for significant enhancement in the number of signal pairs (and, hence, coherent signal dispersion curves) that can be obtained and analyzed in order to characterize the transmitter-channel-receiver system. It should be understood that FIGS. 5B and 5C illustrate just one idealized example of a frequency division multiplexing scheme. Many others can be used. Further, although code division multiplexing is not illustrated, it too can be used to transmit separable signals at the same or overlapping times.

The transmitter 510 transmits the separable baseband signals $S_{T1x}$ and $S_{T1y}$, up-converted to the RF carrier frequency, via the antenna T1. The $S_{T1x}$ signal is transmitted via the x-polarized component of the transmitting antenna T1, while the $S_{T1y}$ signal is transmitted via the y-polarized component of the transmitting antenna. (It is also possible that the signals can be transmitted using different weighted combinations of the x- and y-polarization modes.) The frequency-selective channel (in this example, a multipath channel) includes one or more targets 530 which create multiple signal paths to the receiving antennas R1, R2. These multiple signal paths result in multipath propagation effects that cause different modified versions of the separable transmitted signals $S_{T1x}$ and $S_{T1y}$ to be received at the spatially-separated, dual polarized receiving antennas R1, R2.

The first receiving antenna R1 detects orthogonally-polarized components of the received RF signals. The signal notation $S_{R1u}^{T1x}$ can be used to represent the u-polarized component of the detected signal at the first receiving antenna R1 due to the transmitted signal $S_{T1x}$, while the signal $S_{R1v}^{T1x}$ represents the v-polarized component of the detected signal at the first receiving antenna R1 due to the transmitted signal $S_{T1x}$. In this notation, for any given received signal the subscript indicates the receiving antenna and polarization channel whereas the superscript indicates the transmitted signal which excited that particular received signal. Using this notation, the u- and v-polarization components detected at R1 due to the transmitted signal $S_{T1y}$ can be written as $S_{R1u}^{T1y}$ and $S_{R1v}^{T1y}$, respectively. Similarly, the u- and v-polarization components detected at R2 due to the transmitted signal $S_{T1x}$ can be written as $S_{R2u}^{T1x}$ and $S_{R2v}^{T1x}$, respectively. And the u- and v-polarization components detected at R2 due to the transmitted signal $S_{T1y}$ can be written as $S_{R2u}^{T1y}$ and $S_{R2v}^{T1y}$, respectively.

These signals can be processed at the receiver 520 in order to determine information about the transmitter-channel-receiver system. Part of the processing that can be performed by the receiver 520 is separating the signal responses at each of the four antenna inputs which are attributable to each of the transmitted signals $S_{T1x}$ and $S_{T1y}$. For example, the response at the u-polarization component of the first receiver antenna R1 will, in general, consist of a superposition of channel-modified versions of the transmitted signals $S_{T1x}$ and $S_{T1y}$ transmitted at both the x- and y-polarizations, respectively. The same will generally be true of the response at the v-polarization component of the first receiving antenna R1 and of the u- and v-polarization components of the second receiving antenna R2. The receiver 520 can perform signal separation operations to isolate the response at each receiver input that is attributable to each of the transmitted signals.

In the case where the transmitted signals $S_{T1x}$ and $S_{T1y}$ are made separable using frequency division multiplexing (as shown in FIGS. 5B and 5C), the respective signals $S_{T1x}$ and $S_{T1y}$ which are received at the u-polarization component of the first receiving antenna R1 can be obtained by isolating the frequency components respectively used by each of the transmitted signals. The same can be done for the signals received at the other three receiver inputs. Of course, the particular signal separation operations that are performed will be dependent upon the technique (e.g., time division multiplexing, frequency division multiplexing, and/or code division multiplexing) used at the transmitter 510 to make the transmitted signals separable. Techniques are known in the art for separating signals which have been combined using these multiplexing techniques, as well as other techniques such as eigendecomposition or singular value decomposition techniques. Any such separation techniques can be employed by the receiver 520.

In summary, for cases where the transmitter 510 transmits multiple signals, the detected response at each input port of the receiver 520 will in general consist of the superposition of transmitter-, receiver-, and/or channel-modified versions of each of the multiple transmitted signals (especially if the multiple transmitted signals are coincident in time). The signal separation operations performed by the receiver 520 isolate these superimposed signals in order to determine the individual response at each polarization component of each receiver antenna which is attributable to each transmitted signal. In the case of the system 500 in FIG. 5A, the outputs of the signal separation operations will be the $S_{R1u}^{T1x}$, $S_{R1v}^{T1x}$, $S_{R1u}^{T1y}$, $S_{R1v}^{T1y}$, $S_{R2u}^{T1x}$, $S_{R2v}^{T1x}$, $S_{R2u}^{T1y}$, and $S_{R2v}^{T1y}$ signals. As discussed herein, the receiver 520 can coherently sample and process these signals to determine information about the transmitter-channel-receiver system, including one or more targets located in the channel.

The receiver 520 can down-convert the $S_{R1u}^{T1x}$, $S_{R1v}^{T1x}$, $S_{R1u}^{T1y}$, $S_{R1v}^{T1y}$, $S_{R2u}^{T1x}$, $S_{R2v}^{T1x}$, $S_{R2u}^{T1y}$, and $S_{R2v}^{T1y}$ signals and perform analog-to-digital conversion. This is done using the down-converters 522a-d and the analog-to-digital converters 524a-d. Each of these components can be connected to, and controlled by, a common local oscillator 528 and/or clock signal (as applicable depending upon the circuitry) in order to maintain consistent phase and/or timing references. For example, the signals can be down-converted using a consistent phase reference and the analog-to-digital converters can take synchronous samples. This helps to ensure that relative phase information between the input signals is preserved in the digitized signals. In addition, the signal lines 526a-d from the local oscillator 528 to these signal components can be matched so as to further help maintain phase coherency in the receiver. Although FIG. 5A illustrates a single local oscillator 528, multiple oscillators can be used if they are synchronized. The digital signals that are output from the analog-to-digital converters 524a-d can be saved in a memory 540 and sent to a processor 550 for analysis. Though not illustrated, the receiver 520 can also include signal conditioning circuitry, such as amplifiers, filters, etc. In addition, the receiver 520 could include an intermediate frequency (IF) processing stage.

In some embodiments, the received signals are coherently received and analyzed. Phase information can be preserved between the various received signals. For example, the received signals can share a common local oscillator 528 used in the down-conversion processing and the signals can be synchronously sampled during digital conversion. Coherence at the receiver may entail synchronization of the signal channels in various forms, which can include: phase synchronization; frequency synchronization, sampling synchronization; and local oscillator synchronization in frequency, time, and/or phase. In some embodiments, the receiver 520 can also be coherent with the transmitter 510. For example, the transmitter 510 and the receiver 520 could share a common phase reference such as a local oscillator (e.g., as in a monostatic embodiment where the transmitter and receiver are housed together). (This can provide additional ways to characterize the transmitter-channel-receiver system by enabling, for example, the characterization of Doppler spreads induced in the system.) Additionally, it may be desirable that the receiver signal channels are gain and phase matched (from the antennas to the analog-to-digital converters) across all frequency components of interest and that the local oscillator signal gains to each channel are substantially matched. In some embodiments, the receiver 520 can advantageously achieve precise control of the phase, amplitude, sampling, and frequency among the various receiver channels.

As already mentioned, the receiver channels can be phase and/or gain matched. In some cases, the phase and/or gain matching can be dynamically adjusted. This can be accomplished using phase shifting elements and/or amplifiers in each receiver channel. In some embodiments, these phase shifting elements and/or amplifiers can be adjustable based on, for example, a calibration control input. The calibration control input can be obtained by passing a calibration signal through the various receiver processing channels. The effect of each processing channel on the calibration signal can then be determined. A calibration control input can be generated in order to reduce or eliminate differences between the effects that each processing channel has on the calibration signal. For example, a calibration control input can be generated in order to reduce or eliminate differences between the respective gains of the receiver channels and/or to reduce or eliminate phase differences between the channels. In addition, the phase and/or gain matching can be temperature compensated to help reduce phase and/or gain mismatches which may be induced at different operating temperatures. Digital compensation of the digitized signals can also be employed to achieve phase and/or gain matching.

Although the receiver 520 in FIG. 5A is shown in more detail than the receivers in preceding figures, each of the receivers discussed herein can include elements and features similar to those discussed with respect to the receiver 520 in order to coherently receive and analyze the received signals.

Once, the $S_{R1u}^{T1x}$, $S_{R1v}^{T1x}$, $S_{R1u}^{T1y}$, $S_{R1v}^{T1y}$, $S_{R2u}^{T1x}$, $S_{R2v}^{T1x}$, $S_{R2u}^{T1y}$, and $S_{R2v}^{T1y}$ signals are down-converted and sampled, the respective frequency component phases and amplitudes for various signal pairs can be compared as a means of learning information about the transmitter-channel-receiver system. The different signal pairs are described below with respect to FIG. 5D.

FIG. 5D is a table which lists the signal pairs whose frequency component phases and/or amplitudes can be compared to determine coherent signal dispersion information for the system 500 shown in FIG. 5A. As already discussed, the system 500 in FIG. 5A includes two transmitter channels (from one dual polarized transmitting antenna) and four receiver channels (which are obtained from spatially-separated dual polarized antennas). As shown in the table of FIG. 5D, the system 500 provides as many as 44 signal pairs whose respective frequency component phases and/or amplitudes can be compared in order to determine information about the transmitter-channel-receiver system.

The first six signal pairs in FIG. 5D are formed by the various combinations of the received signals at the first and second receiver antennas R1, R2 which are attributable to the first transmitted signal, $S_{T1x}$. These are $S_{R1u}^{T1x}$, $S_{R1v}^{T1x}$, $S_{R2u}^{T1x}$, and $S_{R2v}^{T1x}$. Signal pairs 1-2 are each made up of orthogonally-polarized components detected at a single one of the receiving antennas R1, R2. In both of these cases, polarization information can be obtained by comparing the respective frequency component phases and/or amplitudes for the signals in each pair.

Additional non-polarization information about the multipath channel can be obtained by also comparing respective frequency component phases and/or amplitudes from signals detected at different antennas. Signal pairs 3-6 in FIG. 5D can be formed to make these cross-antenna comparisons. They consist of the two u-polarization signals that result from the first transmitted signal $S_{T1x}$, which are $S_{R1u}^{T1x}$ and $S_{R2u}^{T1x}$; the two v-polarization signals that result from the first transmitted signal $S_{T1x}$, which are $S_{R1v}^{T1x}$ and $S_{R2v}^{T1x}$; the u-polarization signal from the first antenna and the v-polarization signal from the second antenna that result from the first transmitted signal $S_{T1x}$, which are $S_{R1u}^{T1x}$ and $S_{R2v}^{T1x}$; and finally the v-polarization signal from the first antenna and the u-polarization signal from the second antenna that result from the first transmitted signal $S_{T1x}$, which are $S_{R1v}^{T1x}$ and $S_{R2u}^{T1x}$. The values which result from these cross-antenna comparisons of the respective frequency component phases and/or amplitudes of received signals resulting from the same transmitted signal S n. (i.e., the values calculated from signal pairs 3-6 in the table shown in FIG. 5D) are not polarization values. Nevertheless, they can include important information about the transmitter-channel-receiver system, including one or more objects within the channel.

The second six signal pairs in FIG. 5D are formed by the various combinations of the received signals at the first and second receiver antennas R1, R2 which are attributable to the second transmitted signal, $S_{T1y}$. These are $S_{R1u}^{T1y}$, $S_{R1v}^{T1y}$, $S_{R2u}^{T1y}$, and $S_{R2v}^{T1y}$. Co-antenna signal pairs are those made up of orthogonally-polarized components detected at a single one of the receiving antennas R1, R2. These are signal pairs 7 and 8 in FIG. 5D. Comparisons of the respective frequency component phases and/or amplitudes for these signal pairs can yield polarization information. However, additional, non-polarization information can also be obtained from the cross-antenna signal pairs. These are signal pairs 9-12 in FIG. 5D.

The next 16 signal pairs in FIG. 5D (i.e., signal pairs 13-28) are formed by separately pairing each of the four received signals attributable to the first transmitted signal (i.e., $S_{R1u}^{T1x}$, $S_{R1v}^{T1x}$, $S_{R2u}^{T1x}$, $S_{R2v}^{T1x}$) with each of the four received signals attributable to the second transmitted signal (i.e., $S_{R1u}^{T1y}$, $S_{R1v}^{T1y}$, $S_{R2u}^{T1y}$, and $S_{R2v}^{T1y}$). Specifically, signal pairs 13-16 represent the comparison of the u-polarization component detected at the first receiving antenna R1 due to the first transmitted signal $S_{T1x}$ with each of the received signals (detected at both the first and second receiving antennas R1, R2) that are attributable to the second transmitted signal $S_{T1y}$. Signal pairs 17-20 represent the comparison of the v-polarization component detected at the first receiving antenna R1 due to the first transmitted signal $S_{T1x}$ with each of the received signals (detected at both the first and second receiving antennas R1, R2) that are attributable to the second transmitted signal $S_{T1y}$. Signal pairs 21-24 represent the comparison of the u-polarization component detected at the second receiving antenna R2 due to the first transmitted signal $S_{T1x}$ with each of the received signals (detected at both the first and second receiving antennas R1, R2) that are attributable to the second transmitted signal $S_{T1y}$. Finally, signal pairs 25-28 represent the comparison of the v-polarization component detected at the second receiving antenna R2 due to the first transmitted signal $S_{T1x}$ with each of the received signals (detected at both the first and second receiving antennas R1, R2) that are attributable to the second transmitted signal $S_{T1y}$. Thus, each of these signal pairs represents what can be termed a "cross-transmitted signal" comparison. But some are co-antenna, cross-transmitted signal comparisons, while others are cross-antenna, cross-transmitted signal comparisons. None of these signal pairs yields polarization information when the respective frequency component amplitudes and/or phases are compared. Nevertheless, they can yield useful information about the transmitter-channel-receiver system, including a target located in the channel.

The first 28 signal pairs in the table shown in FIG. 5D are made up of only the received signals. However, still additional non-polarization information about the multipath channel can be obtained by comparing each of the eight received signals $S_{R1u}^{T1x}$, $S_{R1v}^{T1x}$, $S_{R1u}^{T1y}$, $S_{R1v}^{T1y}$, $S_{R2u}^{T1x}$, $S_{R2v}^{T1x}$, $S_{R2u}^{T1y}$, and $S_{R2v}^{T1y}$ with each of the two original transmitted signals $S_{T1x}$ and $S_{T1y}$. These are signal pairs 29-44 shown in the table in FIG. 5D. Specifically, signal pairs 29-32 represent the comparison of the first transmitted signal $S_{T1x}$ with each of the four received signals that are attributable to it (i.e., $S_{R1u}^{T1x}$, $S_{R1v}^{T1x}$, $S_{R2u}^{T1x}$, and $S_{R2v}^{T1x}$). Signal pairs 33-36 represent the comparison of the first transmitted signal $S_{T1x}$ with each of the four received signals that are attributable to the other transmitted signal $S_{T1y}$ (i.e., $S_{R1u}^{T1y}$, $S_{R1v}^{T1y}$, $S_{R2u}^{T1y}$, and $S_{R2v}^{T1y}$). Signal pairs 37-40 represent the comparison of the second transmitted signal $S_{T1y}$ with each of the four received signals that are attributable to the other transmitted signal $S_{T1x}$ (i.e., $S_{R1u}^{T1x}$, $S_{R1v}^{T1x}$, $S_{R2u}^{T1x}$, and $S_{R2v}^{T1x}$). Finally, signal pairs 41-44 represent the comparison of the second transmitted signal $S_{T1y}$ with each of the four received signals that are attributable to it (i.e., $S_{R1u}^{T1y}$, $S_{R1v}^{T1y}$, $S_{R2u}^{T1y}$, and $S_{R2v}^{T1y}$).

While FIG. 5A illustrates a system 500 with two transmitter channels from a single dual polarization antenna, the two transmitter channels could alternatively be connected to two spatially-separated antennas. In fact, the system could include an arbitrary number of spatially-separated transmitter antennas, and each of those could be dual polarized to provide two transmitter channels each. Further, while the system 500 illustrated in FIG. 5A includes two receiver antennas, it could include any arbitrary number of spatially-separated receiver antennas, including a single receiver antenna. Again, each of those could be dual polarized to provide two receiver channels each. Systems with larger numbers of transmitter and receiver channels can provide larger numbers of coherent signal dispersion curves. For example, a four-transmitter-channel by four-receiver-channel system could provide over 100 coherent signal dispersion curves for analysis. It should be understood, however, that systems such as those illustrated herein can include an arbitrary number of coherent transmitter channels and an arbitrary number of coherent receiver channels. In addition, tri-polarized antennas could be used by the transmitter and/or receiver so as to allow for the transmission or reception of electric fields from any direction.

While separate transmitter and/or receiver signals have been described herein as being associated with the individual outputs of separate antenna ports, it is not required that each transmitted signal correspond only to what is sent via a single antenna or that each received signal correspond only to what is received via a single antenna. For example, instead of employing antenna ports as the fundamental quantity, beams derived from a weighted combination of antenna elements (on the transmitter and/or receiver side) can be used instead. In such cases, each beam can be treated as one of the transmitter/receiver signals for purposes of the analysis described herein. This is one of the benefits of a coherent system. In fact, these beams can even be frequency dependent. For a linear combination of spatially-separated antennas, frequency-dependent weights could correspond to different beam steering directions as a function of frequency. For linear combinations of a single dual polarized antenna, frequency-dependent weights would generally correspond to different polarizations as a function of frequency. For an antenna system with both space and polarization separated elements, a weighted combination involving space and polarization dimensions can be used.

While FIGS. 1, 2A, 3A, 4A, and 5A all illustrate bistatic transmitter/receiver configurations, in other embodiments, they could each be monostatic configurations. Furthermore, although the transmitters and receivers have been described herein as each using different antennas, one or more antennas could be shared in common by both a transmitter and a receiver (e.g., as in a monostatic system). For these cases, to improve isolation between the transmitter and the receiver when operating simultaneously, a circulator (or other circuit to mitigate the impact of transmissions on the receiver) can be employed. In the case that multiple separable transmitter signals are employed, although each receiver signal will be subject to interference from the transmitter signal coupled to the common antenna (attenuated by the isolation circuit), the signals of interest from the other transmitter signals can be orthogonal, thereby facilitating reception of separable signals at the receiver.

In addition, although FIGS. 2, 3A, 4A, and 5A use RF signals to make the measurements described herein, it should be understood that the concepts can equally apply to other types of signals, including signals carried by various types of electromagnetic radiation such as infrared or visible light signals, ultraviolet signals, or x-ray signals. In addition, the concepts described herein can apply to transmission lines or to signals carried by other types of wave phenomena besides electromagnetism, such as acoustic signals, etc. Furthermore, in place of, or in addition to antennas to measure the electric field, alternative sensors could be employed to measure the magnetic field. Thus, the systems described herein can be adapted to operate using different types of signals.

Figure 6:
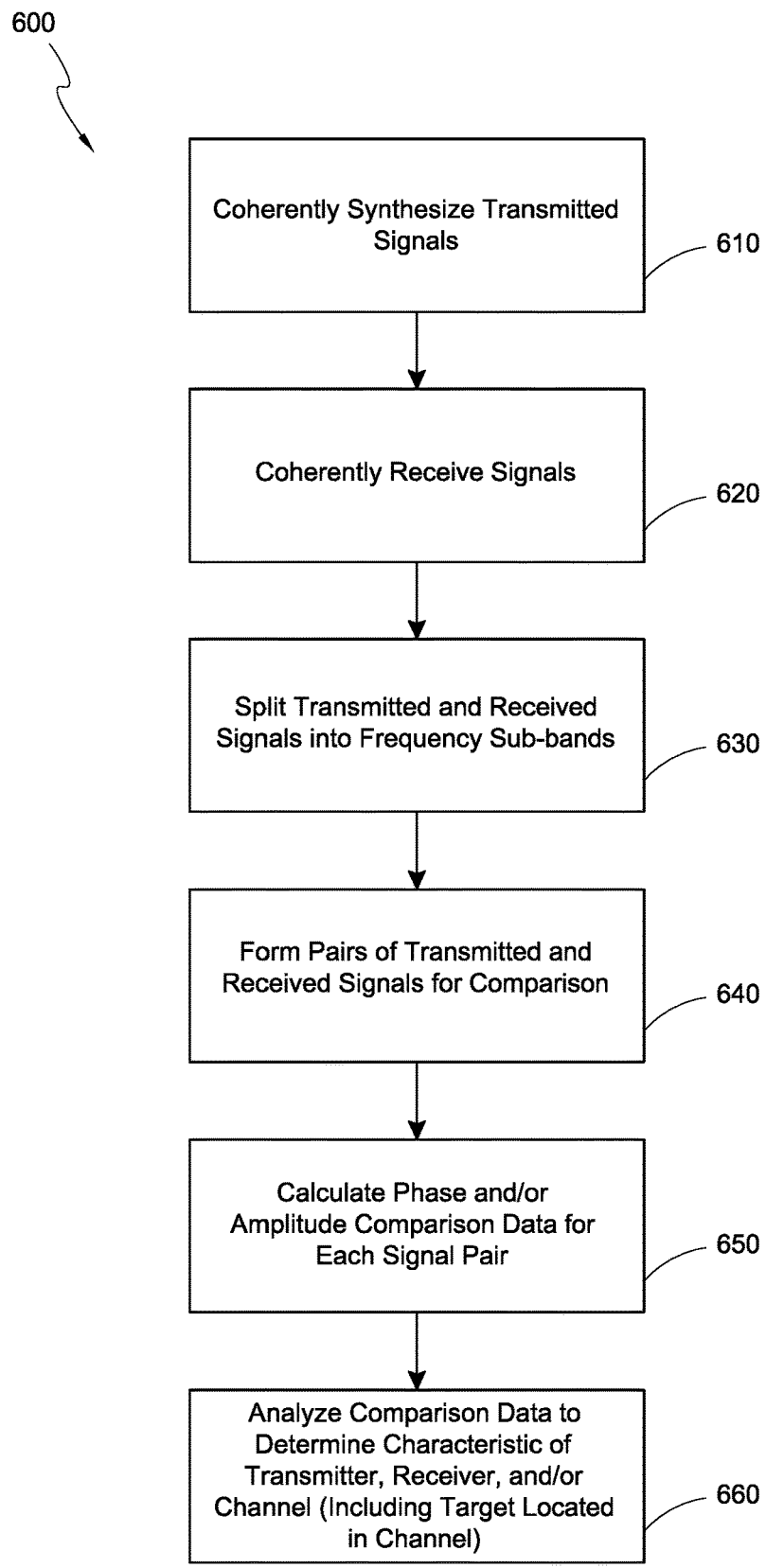
FIG. 6 illustrates an example method for conducting coherent signal analysis using transmitted and received signals from, for example, the system of FIG. 5A.

FIG. 6 illustrates an example method 600 for conducting coherent signal analysis using transmitted and received signals from, for example, the system 500 of FIG. 5A. The method 600 begins at block 610 where multiple transmit signals are coherently synthesized, for example as discussed with respect to FIG. 5A. These transmit signals can be sent through a channel to a receiver (e.g., receiver 520). At block 620, multiple signals are received after having propagated through a channel, such as a multipath channel. As discussed further herein, in some embodiments, the transmitter and/or receiver antennas can be positioned in proximity to the body of a medical patient or other subject such that the propagation channel includes at least part of the patient's, or other subject's, body. The signals can be received using two or more spatially-separated receiver antennas. The receiver antennas can be dual polarized. The received signals can result from one or more transmitted signals (e.g., using transmitter 510). The received signals can be coherently received and analyzed (e.g., coherently down-converted and synchronously sampled), for example as discussed with respect to FIG. 5A. In the case where the received signals result from multiple separable transmitted signals, this processing can include performing signal separation operations to isolate the received signals that are attributable to each transmitted signal. The coherent sampling and processing preferably preserves phase information between the various received signals. In addition, if a phase reference is shared between both the transmitter and receiver (as would be possible using a shared local oscillator in a monostatic configuration), then phase information can be preserved between transmitted and received signals.

At block 630, the transmitted and received signals from blocks 610 and 620 can each be separated into frequency sub-bands. This can be done using, for example, a Fourier transform or other processing.

At block 640, multiple pairs of received and transmitted signals are formed. FIG. 5D illustrates examples of these signal pairs. In general, the signal pairs can be formed between received signals only, or between received signals and transmitted signals. When signal pairs between received signals and transmitted signals are formed, these can include pairs which include a received signal and the particular transmitted signal to which the received signal is attributable, or pairs which include a received signal and a transmitted signal other than the one to which the received signal is attributable. Signal pairs can be formed between received signals detected at the same antenna or at different antennas. Signal pairs can be formed between received signals that have the same polarization or different polarizations. In addition, signal pairs can be formed between received signals that are attributable to the same transmitted signal or between received signals that are attributable to different transmitted signals.

At block 650, frequency component phase and/or amplitude comparison data can be calculated for each signal pair from block 640 and for each frequency sub-band from block 630. For example, the amplitudes of the frequency components of one of the signals can be compared to those of the other by calculating differences between the respective amplitudes or ratios of the amplitudes. Similarly, the phases of the frequency components of one of the signals can be compared to those of the other by calculating differences between the respective phases. Other computations can also be useful in comparing these magnitudes and phases. For example, in some embodiments, calculation of the phase and/or amplitude comparison data is accomplished by calculating a Jones vector or Stokes parameters (normalized or unnormalized) for each sub-band of each signal pair. (Again Stokes parameters ($S_0$, $S_1$, $S_2$, and $S_3$) for each sub-band can be calculated according to the following equations: $S_0 = (Y_1 \cdot Y_1^*) + (Y_2 \cdot Y_2^*)$; $S_1 = (Y_1 \cdot Y_1^*) - (Y_2 \cdot Y_2^*)$; $S_2 = (Y_1 \cdot Y_2^*) + (Y_2 \cdot Y_1^*)$; and $S_3 = (Y_1 \cdot Y_2^*) - j(Y_2 \cdot Y_1^*)$, where $Y_1$ is a complex number with amplitude and/or phase information for a first signal in the pair of signals being compared and $Y_2$ is a complex number with amplitude and/or phase information for a second signal in the pair of signals being compared.) Although these computations are traditionally used to determine polarization states, they can also be applied as an analytical tool even in cases where the signal pairs are such that the computations do not result in polarization information. As discussed herein, the set of per sub-band comparison values for each signal pair can be referred to as a coherent signal dispersion (CSD) curve or a polarization mode dispersion (PMD) curve, depending on the particular signal pair.

As just mentioned, for each signal pair obtained from any system architecture described herein, Jones vectors or Stokes vectors can be formed. The representation for the former can be written as a complex scale factor (amplitude and phase) that multiplies a unit Jones vector. If relative amplitude and relative phase alone are of interest (such as in characterizing polarization states on a unit sphere), the complex scale factor can be ignored, although the amplitude and phase information provided by the complex scale factor can potentially be useful for sensing and other applications. Stokes vectors of the form $[S_0\ S_1\ S_2\ S_3]$ can be formed for each signal pair using, for example, the equations provided herein. This unnormalized form of a Stokes vector may or may not have a degree of polarization of unity (i.e., where the square of $S_0$ equals the sum of the squares of $S_1$, $S_2$, and $S_3$). In some embodiments, however, the sub-band spacing can be chosen so that the degree of polarization is near unity. In some cases, it may be appropriate to normalize the $[S_1\ S_2\ S_3]$ vector (e.g., so that the sum of the squares of $S_1$, $S_2$, and $S_3$ equals the square of $S_0$, which essentially "forces" the condition of having unit degree of polarization). When plotting the CSD or PMD curves in any of these cases, the 3D locus will not be constrained to a unit sphere, but in some cases, it may useful to normalize the $[S_1\ S_2\ S_3]$ vectors to have unit magnitude so that the CSD or PMD curves will be constrained to a unit sphere. In the case of PMD, this is equivalent to considering the polarization state (i.e., the relative amplitude and relative phase between the signals associated with the signal pair). Since these representations deal primarily with relative amplitude and relative phase information, some amplitude and phase information (a complex scale factor) is not retained through this representation. For all of the cases, it may be useful to retain amplitude and/or phase information associated with the signal pairs that might otherwise be lost in a particular representation. The amplitude and phase can be relative to some reference used to measure these values.

Calculation of a set of Stokes parameters for each sub-band results in a Stokes vector for each sub-band. (Again, although the same equations may be used for calculating Stokes vectors for CSD signal pairs as for PMD signal pairs, the Stokes vectors for CSD signal pairs do not consist of polarization information). If the Stokes vectors (and hence the curves) are not normalized to unit magnitude, the vectors contain amplitude information (e.g., the $S_0$ term in the Stokes vector provides amplitude information) that can be utilized in addition to phase information to analyze the signals. The resultant CSD (or PMD) curve from non-normalized Stokes vectors would not necessarily be constrained to reside on a unit sphere. In some cases, CSD and PMD curves may be continuous. However, in some cases, the resulting curve is a locus of points that may not be continuous. For example, if the transmit polarization is varied with sub-band, or more generally, if the relative amplitude and phase between transmit ports is varied with sub-band, the resulting curve may exhibit discontinuities.

For each signal pair, frequency component amplitude and/or phase comparisons can be made between the signals for different relative delays (e.g., where one of the signals is delayed by one or more samples), or for different frequency offsets (for example where the subcarriers of the two signals are not the same, but are intentionally offset). These offsets in delay and frequency can also be considered simultaneously (e.g., offsets in delay and in frequency). Such characterizations may be useful to establish decorrelation times and decorrelation frequencies. Furthermore, a signal pair consisting of a receiver signal and a transmitter signal could use a delay difference for the signals to align them in time for comparison purposes. Signal cross-correlation, for example, could be used to identify the delay that should be used to align the transmitter signal with the receiver signal.

Dynamic CSD curves can be determined by applying the just-described technique repeatedly over time. This can be done by extracting a time window of data of a desired length from the pairs of received/transmitted signals. Then, for each time window, the frequency component phase and/or amplitude comparison data can be calculated for each frequency sub-band. The time window can then be advanced and the per sub-band comparison values can be calculated once again. This process can be repeated as long as desired in order to determine the time domain behavior of the CSD curves. The length of the time window for each of these iterations can be selected, for example, based upon the timescale of the time-varying effects that are to be analyzed.

Figure 7:
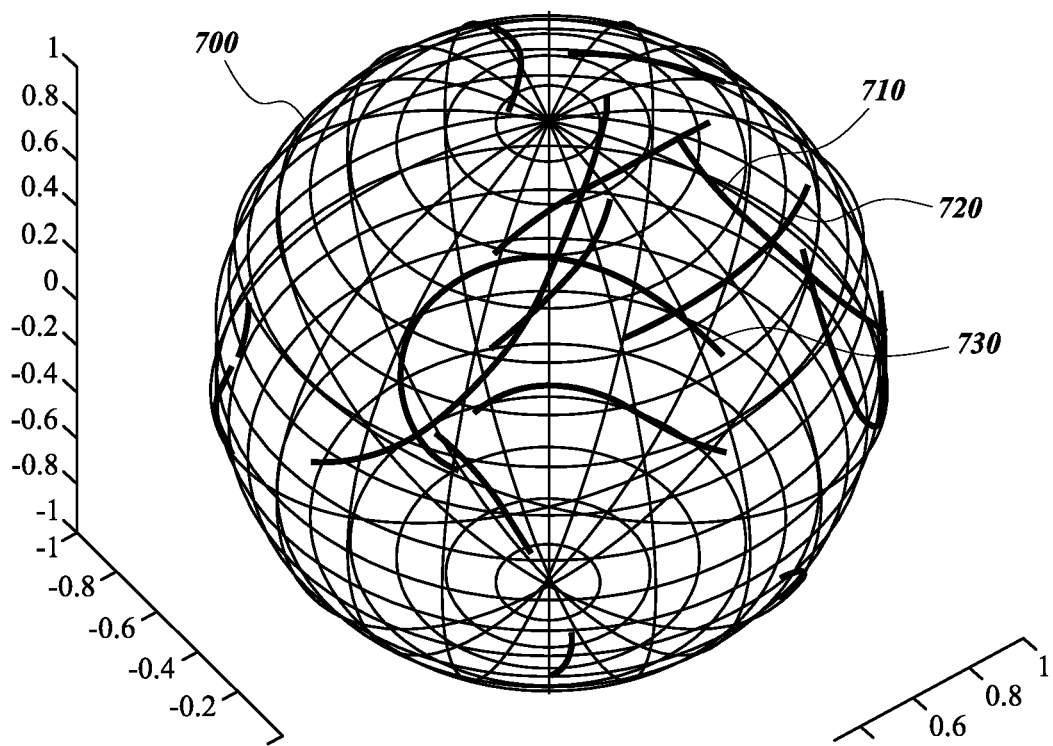
FIG. 7 illustrates example coherent signal dispersion curves on a sphere.

At block 660, the frequency component phase and/or amplitude comparison data (e.g., coherent signal dispersion (CSD) curves) from block 650 can be analyzed in order to determine a characteristic of the transmitter, receiver, and/or channel, including a characteristic of a target located in the channel. In some embodiments, this analysis can include visualization by plotting the per sub-band comparison data for each signal pair on or about a sphere or other manifold. FIG. 7 illustrates example coherent signal dispersion curves 710, 720, 730 on a sphere 700. As previously discussed herein, a Poincaré sphere traditionally has been used to visualize polarization states. Each point on the Poincaré sphere traditionally corresponds to a different polarization state. And points on opposite sides of the sphere traditionally correspond to orthogonal polarization states. However for signal pairs that do not yield polarization information, the representations correspond to a different quantity. Notwithstanding the fact that the coherent signal dispersion curves 710, 720, 730 described herein do not relate to polarization information, they can still be plotted on or about a unit sphere similar to a Poincaré sphere 700 as a useful visualization technique.

The analysis in block 660 can include identifying a characteristic of the comparison data from block 660 at a given time (e.g., length, shape, location on the sphere of a CSD curve, etc.). A characteristic of interest can be identified by, for example, relating the comparison data to calibration data or previously-elicited comparison data. Additionally, the analysis can include identifying a change in a characteristic of the comparison data as a function of time (e.g., length, shape, location on the sphere of a CSD curve, etc.). A characteristic of the comparison data may correspond to a physical characteristic of the system. For example, the length of a CSD curve may be reflective of temporal dispersion between channels; the complexity of a CSD curve may be indicative of the multipath composition; and periodic oscillations may reflect periodic processes in the transmitter-channel-receiver system. Any of these properties, or others, of the comparison data can be analyzed. These analyses can be conducted in the time domain, spatial domain, and/or frequency domain. For example, assume that a target within the channel vibrates at a frequency, $f_v$, while the transmitter and receiver are held stationary. A spectral analysis, perhaps via a discrete Fourier transform, of one or more of the dynamic Stokes parameters calculated from PMD or CSD data should indicate the presence of a frequency component at $f_v$. The magnitude of this $f_v$ component along with the possible presence of other frequency components could provide useful information about said vibrating target. Thus, the spectral analysis can include, for example, determining the magnitude(s) of one or more spectral components of the comparison data from block 660. Many techniques are disclosed in U.S. Patent Publication 2013/0332115 for analyzing polarization mode dispersion curves to obtain useful information about a multipath channel. Notwithstanding the distinctions between polarization mode dispersion curves and coherent signal dispersion curves, the same PMD curve analysis techniques can be applied to the CSD curves disclosed herein. Therefore, U.S. Patent Publication 2013/0332115 is incorporated by reference herein in its entirety for its disclosure of such analysis techniques.

Various operations that can be performed on the coherent signal dispersion curves as part of these analyses include filtering, averaging, statistical analyses, excision, integration, rotation, smoothing, correlation, eigendecomposition, Fourier analyses, and many others.

For some analyses it may be advantageous to reduce each coherent signal dispersion curve to a single value that represents the curve as a whole. This can be done using, for example, a centroiding operation. Experiments have shown that the centroid of a coherent signal dispersion curve can efficiently and effectively reduce unwanted noise while still providing useful information about the transmitter-channel-receiver system.

Estimation techniques can be applied in order to reduce variations in a measured CSD curve. This can be done because there typically is a correlation between the values for neighboring sub-bands in the curve (i.e., the coherence signal dispersion information is not generally expected to exhibit discontinuities from one sub-band to the next). This property of coherent signal dispersion curves allow for the usage of techniques to improve the quality of CSD curve estimates.

Many techniques are disclosed in U.S. Patent Publication 2013/0332115 for analyzing polarization mode dispersion curves to obtain useful information about physical movements of a target object. Notwithstanding the distinctions between polarization mode dispersion curves and coherent signal dispersion curves, the same PMD curve analysis techniques can be applied to the CSD curves disclosed herein. Therefore, U.S. Patent Publication 2013/0332115 is incorporated by reference herein in its entirety for its disclosure of such analysis techniques.

One benefit of the CSD curves described herein over the PMD curves described in U.S. Patent Publication 2013/0332115 is the rich diversity of the CSD curves, which far outnumber PMD curves. Owing to the rich diversity of the CSD curves, it becomes much more likely that a given time-varying characteristic of the multipath channel, including a target object in the channel, will be evident in at least one of the CSD curves.

U.S. Patent Publication 2013/0332115 describes many other practical applications of PMD analysis. It should be understood that the systems and methods described herein for performing CSD can also be applied to any of those applications, likely with improved results. Thus, U.S. Patent Publication 2013/0332115 is incorporated by reference herein for its disclosure of all such practical applications.

Medical Monitoring Using PMD and/or CSD Signals

Figure 8:
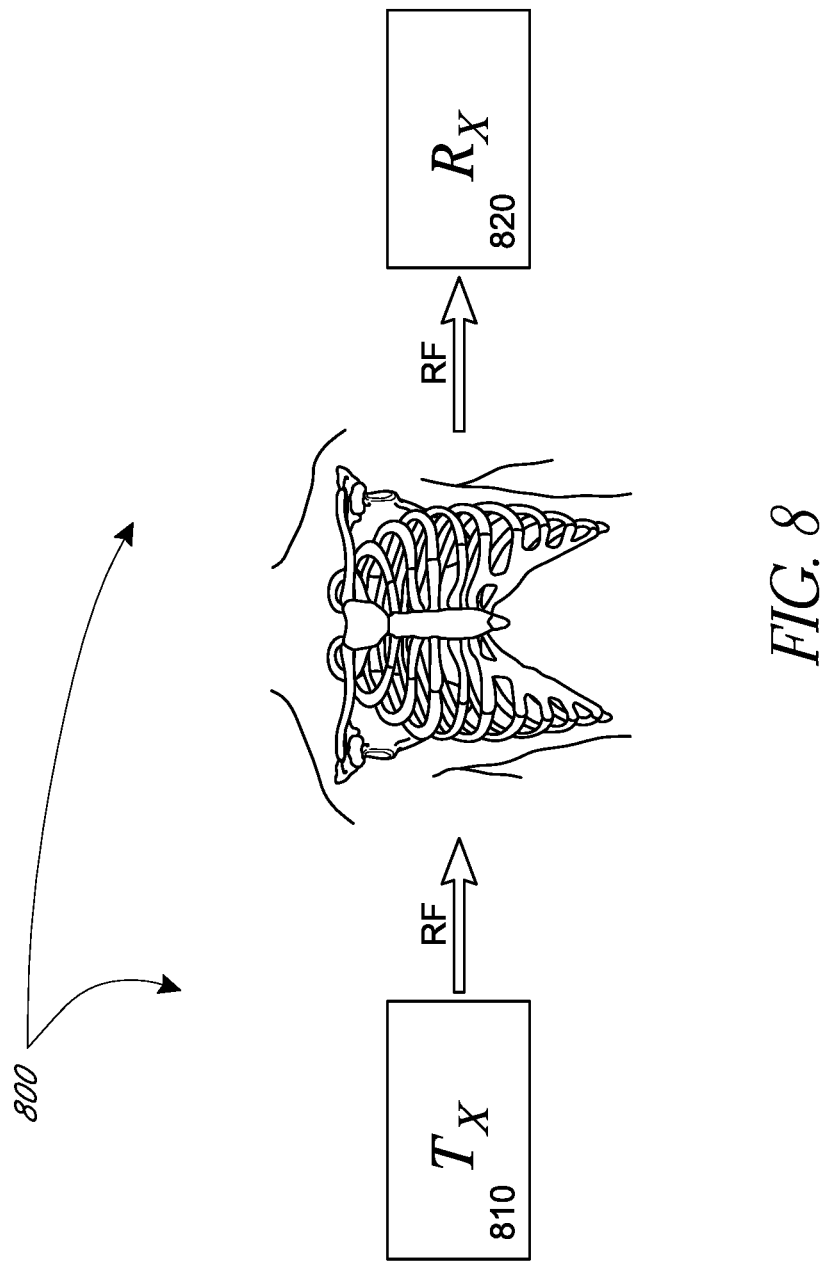
FIG. 8 shows a physiological sensing device that can detect physiological characteristics associated with, for example, a patient's heart and/or lung activity.

Embodiments of the systems described herein (e.g., as shown in FIGS. 1, 2, 3A, 4A, and/or 5A) can be used as physiological sensing devices. This is illustrated in FIG. 8, which shows a physiological sensing device 800 that can detect physiological characteristics associated with, for example, a patient's heart and/or lung activity. Although a human patient is illustrated, the systems and methods described herein can also be used with other subjects, including animal subjects. The physiological sensing device can include a transmitter 810 and a receiver 820. The transmitter 810 can be like any of the other transmitters, with their associated transmit antennas, described herein. Likewise, the receiver 820 can be like any of the other receivers, with their associated receive antennas, described herein. The physiological sensing device 800 can function as the other systems described herein to obtain PMD and/or CSD waveforms.

As shown in FIG. 8, the transmitter 810 can transmit RF waves toward a subject's body, with the RF waves being at least partially reflected, diffracted, scattered, and/or transmitted by the body. The RF signals can at least partially penetrate biological tissues and can be modulated by movements of the internal or external anatomy of the subject's body. The modulated RF signals are then detected by the receiver 820. Although FIG. 8 shows a bistatic configuration, a monostatic configuration can also be used because some of the RF waves may be reflected by the subject's anatomy. In some embodiments, both the transmit antenna(s) and the receive antenna(s) can be positioned within 15 feet of the subject's body, or within 10 feet of the subject's body, or within 5 feet of the subject's body, or within 2 feet of the subject's body. In some embodiments, the transmit and receive antenna(s) can be positioned approximately about opposite sides of the body, separated by 120-180 degrees. In other embodiments, the transmit and receive antennas can be positioned approximately about the same side of the body, separated by 0-120 degrees.

Since the physiological sensing device 800 can use RF waves to detect anatomical movements, it can operate remotely, from a distance, through clothing and other common obstacles, not requiring direct contact with the subject's body. In FIG. 8, the RF waves are shown being transmitted toward the human subject's thorax. Using the RF waves, the physiological sensing device 800 detects physical movements in the thorax associated with the beating heart and/or the respiration of the lungs of the subject. These and other physical movements, including movements of organs, muscles, limbs or other body parts, can be detected by the physiological sensing device 800 because such movements alter the multipath channel between the transmitter 810 and the receiver 820, even when those movements occur inside the subject's body. Those changes to the multipath channel induce changes in PMD and CSD responses, as described herein.

By detecting the physical motions associated with heart and lung activity, the physiological sensing device 800 may provide useful medical information about heart and lung functions which, in some cases, may not be obtainable by conventional means in a typical residential or even clinical setting, thereby aiding in medical treatment and overall health assessments. For example, the physiological sensing device 800 can provide information that may be useful to doctors for monitoring heart-rate, heart rhythm, blood pressure, heart arrhythmias, asynchronous contractions, congestive heart failure, neo-natal heart rate, fetal heart rate, vascular elasticity, mitral valve prolapse, heart contractile and relaxation function, as well as lung respiration rate, lung volume, and detection of cancer in the lungs. Accordingly, the physiological sensing device 800 can provide information useful for diagnosing and/or treating health conditions associated with these and other physiological characteristics. In addition, the physiological sensing device 800 may provide data which is complementary to, and can be compared with, that which may be obtained from conventional medical instruments (e.g., electrocardiograph (ECG), echocardiogram, blood pressure monitoring, magnetic resonance imaging (MRI), computed tomography scans, X-ray scans, etc.). In these embodiments, the waveform(s) from the device 800 can be synchronized with a waveform from the conventional medical instrument to allow better comparison between the data from the different instruments. This can be done by, for example, time shifting one of the waveforms with respect to the other. This complementary information can be used for many purposes, such as to link electrical impulses to actual heart movements or to synchronize imaging scans to precise phases of heart contractions or otherwise supplement the operation of scanning/imaging equipment.

Since the physiological sensing device 800 does not require physical contact with the subject, it is easy to set-up and use. The sensing device 800 can be used in homes, hospitals, doctor's offices, work environments, elderly care facilities, prisons, beds, cars/airplanes/trucks, zoos, animal care facilities, medical research facilities (e.g., with mire and other animals), and for athletics, exercising, and training to name just a few examples. The non-contact physiological sensing device 800 can be capable of monitoring a subject from several feet away or further. Since the device does not require physical contact with the subject in order to function, RF antennas can be positioned in a variety of locations to provide medical personnel with real-time data from, for example, a subject in an examination room, on a hospital bed, or even in the waiting room. The physiological sensing device 800 may also enable inpatient or at-home monitoring of subjects while seated or sleeping. In some embodiments, the transmit and/or receive antennas for the physiological sensing device can be integrated into chairs, beds, walls, floors, ceilings, vehicles, etc. to achieve this.

As describe above, the technology employed by the physiological sensing device 800 can be used to simultaneously obtain many diverse signals (e.g., as represented by the signal pairs in FIGS. 3B, 4B, and 5D), each of which may be well-suited to sensing a particular physiological characteristic. Further, linear combining of these coherent diversity responses can be used to accentuate or suppress parts of the response to aid in a diagnosis of heart and/or lung conditions. This can be accomplished using, for example, any of the combination techniques described herein or in U.S. patent application Ser. No. 15/478,179, filed Apr. 3, 2017, and entitled "LINEAR COMBINATIONS OF TRANSMIT SIGNALS BY A RECEIVER," the entirety of which is hereby incorporated by reference herein.

Figure 9A:
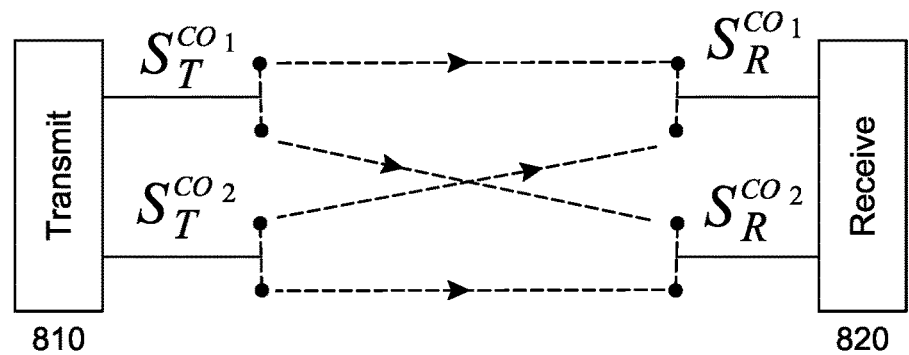
FIGS. 9A-9C illustrate various antenna configurations which can be used by the physiological sensing device of FIG. 8.
Figure 9B:
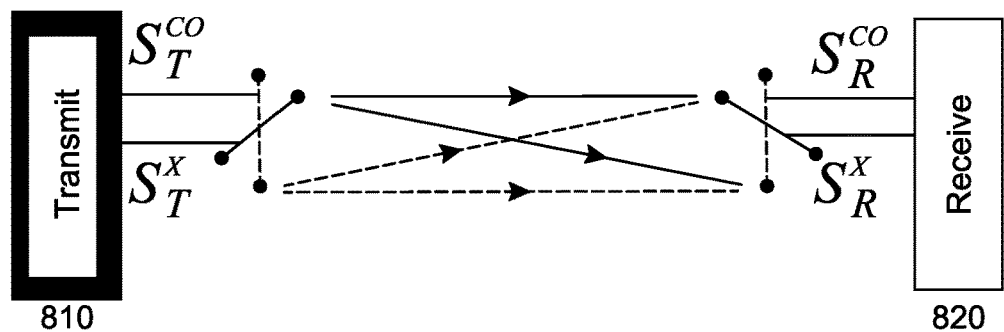
Figure 9C:
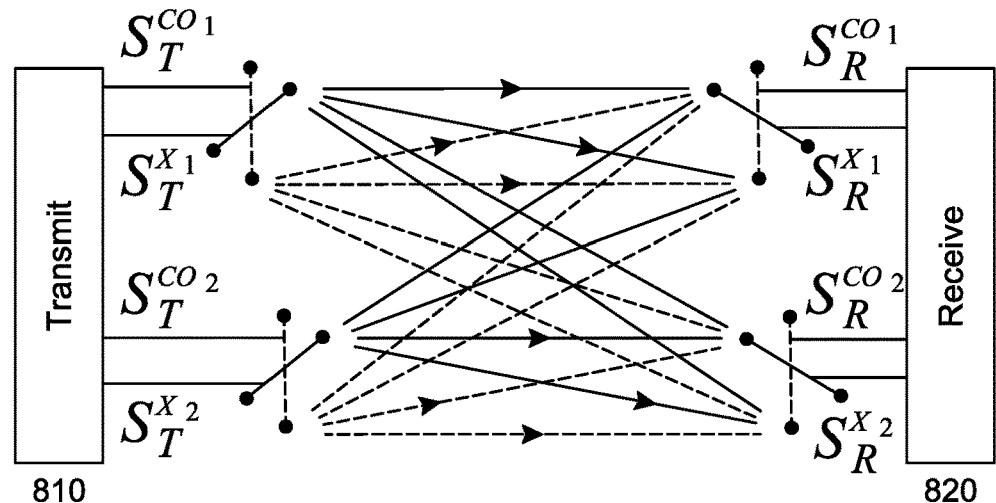

FIGS. 9A-9C illustrate various antenna configurations which can be used by the physiological sensing device 800. These antenna architectures include co-polarized arrays (CP) (FIG. 9A), dual-polarization (DP) architectures (FIG. 9B), and space-polarization (SP) architectures (FIG. 9C). DP architectures can incorporate orthogonally-polarized antenna elements that share a common phase center. In the illustrated embodiment of FIG. 9B, the channel from each emitter to each receiver comprises a 2×2 multiple-input multiple-output (MIMO) frequency-dependent channel, usually with uncorrelated channel responses. The CP architecture in FIG. 9A can incorporate co-polarized antenna elements that are spatially separated, again leading to a 2-2 frequency-dependent MIMO channel for each source. However, in the case of CP architectures, the channel gains may or may not be correlated depending upon the multipath structure, especially the angular spread. The SP architecture illustrated in FIG. 9C incorporates two spatially separated, dual-polarized antennas, leading to channel diversities in both space and polarization. The resulting channel is a 4×4 frequency-dependent MIMO channel, where, again, channel correlations, especially for the space components, will depend upon the multipath structure. In addition, since the transmitter 810 and the receiver 820 can include multiple antennas, they can employ beamforming techniques to transmit or receive any of the signals discussed herein as directional beams. This can be useful in an application where vibration responses from multiple sensors can be used for position localization of a subject. This is possible, for example, using arrays of sensors, where direction of arrival from each node to each vibration frequency (heart rate and/or respiration rate) can be determined via triangulation.

An embodiment of the CP architecture is depicted in FIG. 9A, and incorporates co-polarized antennas that are spatially separated. The channel response is characterized by the two links in the system (from the transmitter to each receive antenna), and the received signal vector is comprised of the convolutions of the transmitted signals with the respective channel impulse responses indexed by time.

An embodiment of the DP architecture is depicted in FIG. 9B. Polarization-based architectures offer potential benefits over CP architectures. First, in space-constrained applications, there may be limits on the number of antennas that can be deployed (e.g., one or two spatially separated antennas), restricting the number of channels in a given deployment. In such cases, one strategy for increasing the number of sensor channels is to employ a dual-polarized antenna at each antenna location. Additionally, the polarization channel responses are largely independent, which can be advantageous for some applications. Unlike the CP architecture, the average powers of the channel response components are typically not identical. The fading statistics and correlations between the sub-channels may also be different than for the CP architecture.

An embodiment of the SP architecture is depicted in FIG. 9C. The SP architecture achieves diversities associated with both DP and CP architectures.

In addition to the transmitter 810, transmit antennas, the receiver 820, and the receive antennas, the physiological sensing device 800 can also include one or more processing, memory, and/or storage devices. The processing devices can be, for example, field-programmable gate arrays (FPGAs), central processing units (CPUs), graphics processing units (GPUs), application-specific integrated circuits (ASICs), digital signal processors (DSPs), or other processing devices which have been configured to carry out signal processing algorithms on the collected data. In some embodiments, the collected data can be stored for later analysis, while in other embodiments the processing devices can carry out real-time analysis of the data. For example, data can be buffered to enable explorations to highlight or identify features of measured responses. This can be accomplished manually (e.g., by a nurse or physician) or automatically by the processing devices to find features of interest. The physiological sensing device 800 can also include one or more input/output devices for receiving user commands and/or outputting results.

Various features of the physiological sensing device 800 can be re-configurable based on, for example, user inputs or automated algorithms. For example, the device can accept parameters for specifying RF transmit power levels, antenna-subject standoff distances and/or relative positioning, RF carrier frequencies, signal bandwidth and sub-bands, sample rate, transmit waveform type or shape, antenna configuration (including the number and type of transmit and receive antennas and any beam forming), receiver data analysis techniques (e.g., digital filters), sub-band combinations, sub-channel combinations, etc. In some embodiments, the carrier frequencies can be adjusted over a range between 10 MHz and 6 GHz, though other embodiments may be capable of frequency tuning over frequencies exceeding 6 GHz. The fact that the physiological sensing device 800 can operate at multiple frequencies provides diversity in penetration depth of the RF waves into the subject's body, as well as diversity in the resulting responses. The difference in depth of penetration for different frequencies can enable forms of imaging that take advantage of the different responses. In some embodiments, the physiological sensing device 800 can operate in the industrial, scientific, and medical (ISM) bands (e.g., near 917 MHz, 2.4 GHz, and 5 GHz). The bandwidth of the transmit signals can also be configurable, for example over a range from 6.25 kHz to 20 MHz. The device 800 can also have 80 dB or more of dynamic range.

Figure 10:
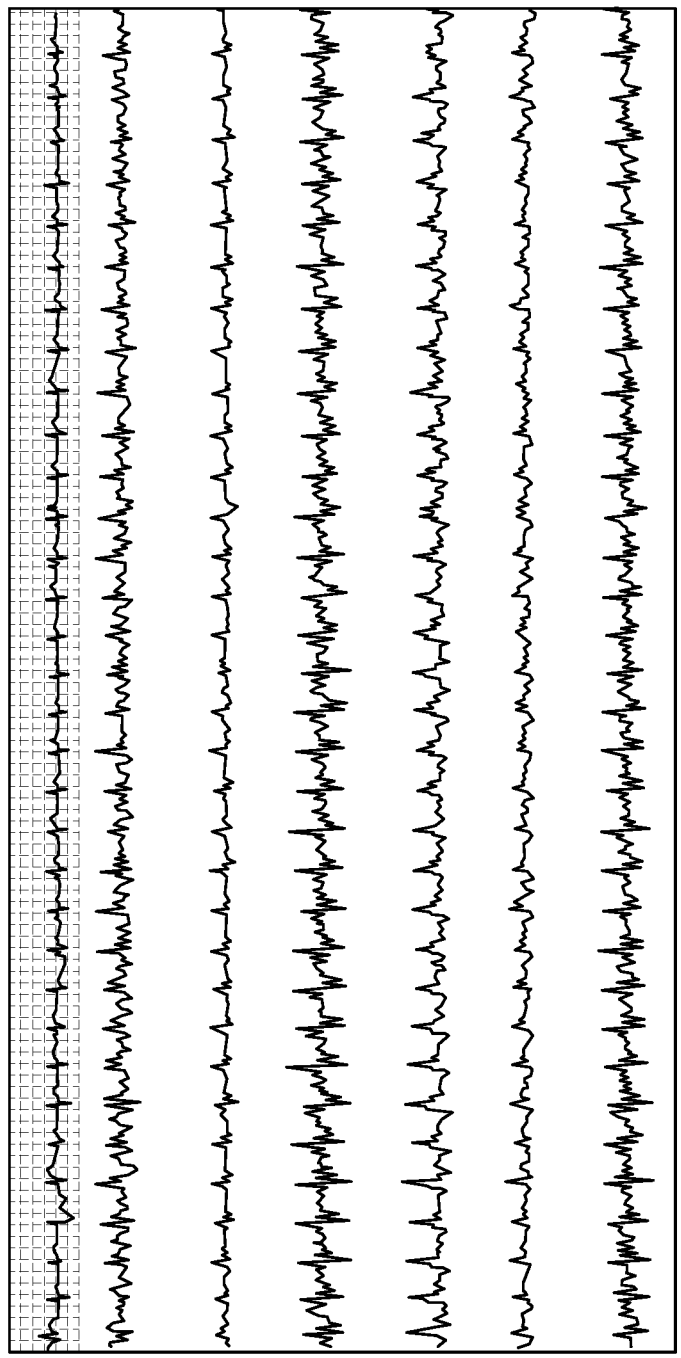
FIG. 10 illustrates example heart waveforms that have been collected from a patient by an embodiment of the physiological sensing device of FIG. 8.

FIG. 10 illustrates example heart waveforms that have been collected from a patient by an embodiment of the physiological sensing device 800. The data collection experiment involved the use of transmitter and receiver antennas that were approximately 3 feet from the human subject. When RF waves are directed into the thorax of the patient, the heart and lung responses may jointly contribute to the RF response. In some cases, it may be desirable to decouple the heart and lung responses. In some embodiments, this can be achieved by designing the transmit waveforms and received data processing to facilitate a wide range of filtering options to separate the heart and lung portions of the cumulative received response. The high level of diversity achieved with the coherent-MIMO physiological sensing device 800 is invaluable in this regard, as some of the various signals may be more dominantly reflective of the patient's heart activity, while others may be more dominantly reflective of the patient's lung activity. In other embodiments, the heart and lung responses can be decoupled by instructing the patient to hold his or her breath while the measurements are taken. In the case of the measurements shown in FIG. 10, the patient was instructed to hold his breath for a duration of about 20 seconds while the measurements from the 2×2 system were taken. By instructing the patient to hold his or her breath, signals related to heart activity can be decoupled from lung activity. In some embodiments, the physiological sensing device 800 can provide an instruction to the patient to begin a breath hold before capturing measurements and to end the breath hold once the measurement process is complete.

FIG. 10 depicts a number of measurement parameters versus time. The periodicity of each trace is an indication that the various measurements are induced by the heart rate. The top waveform in FIG. 10 is an ECG waveform which is compared to six PMD/CSD signals obtained by the device 800. The heart rate can be observed in all of the signals. And additional measurements in combination with the thumb-based single-channel ECG system confirmed that the periodicities were induced by the activity of the heart. Note that in the figure, some of the traces bear some resemblance to ECG waveforms, while others exhibit similar periodicities but with different textures. Each of the signals represents a different "look" at heart-induced responses, using the available diversities. The variations in the signals may be due to various different physiological or anatomical features. These signals can be analyzed using, for example, any of the techniques disclosed herein to extract information regarding a physiological characteristic. To determine heart rate or respiration rate, the processing could include application of a frequency domain transform to determine one or more frequency components of interest (e.g., a fundamental frequency, or dominant frequencies) in the PMD/CSD responses. Measured parameters (time-varying or otherwise), such as those illustrated in FIG. 10, used for sensing physiological characteristics with the device 800 can include the following: the measured field components (electric or magnetic) in time, frequency, or other domains; signal power; polarization and/or coherence parameters (including Stokes parameters); transfer functions measured for each channel; eigenmode parameters; and any other useful parameter that can be derived from the received signals, for example using functions to operate on the signals, such as linear combinations or non-linear operators.

In some embodiments, the physiological sensing device 800 can be used for remotely measuring blood pressure. One way to measure blood pressure is through use of pulse transit time (PTT) measurements (e.g., as discussed in "Cuff-Less and Continuous Blood Pressure Monitoring: a Methodological Review," by Sharma et al., in Technologies 2017, 5(2), 21, which is incorporated by reference herein in its entirety). This can be accomplished using the physiological sensing device 800 by calculating correlations of time-domain PMD/CSD signals that are generated from different parts of the subject's body and then identifying timing response differences due to heart responses from different parts of the subject's body to obtain pulse delay information. By performing auto- and cross-correlation functions on the measured time-domain parameters, the time delay can be estimated, leading to an estimate of the blood pressure. This pulse transit time (PTT) technique for blood pressure monitoring may involve comparing responses from the subject's chest and an appendage, such as the wrist. Also, information from the head, neck and/or other parts of the body (including comparisons of the responses) can also be used.

In some embodiments, the physiological sensing device 800 can be used to detect and monitor a subject's motion activity (e.g., movements of the head, arms, legs, torso, etc.). These movements will induce changes in PMD and CSD responses, which can be sensed by the device 800. This can be used, for example, to monitor sleep apnea, to assess sleep quality, or to assess that the subject is alive (whether the subject is alive can, of course, also be assessed based on monitoring the heartbeat or respiration).

In some embodiments, the physiological sensing device 800 can be used to determine whether the subject is a human or animal. This can be done by sensing one or more differentiating physiological characteristics between human and animal. For example, the device 800 can be used to detect the heart rate of the subject. If the heart rate is within the range of expected human heart rates, then the device 800 can determine that the subject is a human. If the heart rate is outside the range of expected human heart rates, then the device 800 can determine that the subject is some other creature.

The diverse PMD and/or CSD signals which can be collected by the device can be analyzed using deep learning techniques to identify the different physiological or anatomical information which may be present in the diverse signals. For example, groups of subjects with known heart or lung anomalies can be established (e.g., groups of subjects with baseline asymptomatic arrhythmias such as atrial or ventricular ectopic beats that are bigeminal or trigeminal, subjects with contractile and valvular dysfunction, etc.). Then, the physiological sensing device 800 can be used to collect a set of diverse PMD and/or CSD waveforms from each subject. These waveforms can be used as training data for an artificial neural network. Using this training data, the artificial neural network can be trained to identify signal features associated with each of the heart or lung anomalies. This type of processing, which is made possible by the high level of diversity provided by the physiological sensing device 800, can enable detection of heart or lung conditions which would likely not otherwise be recognizable.

In addition, the physiological sensing device 800 can be used to collect PMD and/or CSD waveforms from subjects with persistent rate controlled atrial fibrillation and artificial pacemakers, under the direction and guidance of a cardiac electrophysiologist. An example of a subject with pacemakers that can be used in arrhythmia research is the use of sheep with embedded pacemakers (e.g., transcatheter pacemakers) to study and control heart behavior. Baseline chronic arrhythmias will have variable electromechanical coupling that should be reflected in variability in the beat-to-beat cardiac motion which can be used to assess the sensitivity and specificity of the processed RF signals from the device 800. Implanted devices like artificial pacemakers enable a level of direct control over the heart not possible in other subjects. Observing the physiological sensing device's measurements as changes are made to the implanted device such as rate, right ventricular, left ventricular or biventricular pacing can be used to highlight cause-effect relationships. Also, heart-monitoring data taken directly from the implanted device can be correlated to the measured responses from the device 800 for further corroborating evidence. Measurements of the device 800 can also be used to assess any differences in signal intensity or pattern between subjects with normal and reduced left ventricular ejection fraction.

Traditional and non-traditional medical characteristics that may be directly or indirectly derived from the waveforms collected by the physiological sensing device 800 include: heart rate and rhythm, ECG matching of arrhythmias, heart contractile function, heart valve function, heart relaxation/diastology, neo-natal heart rate, fetal heart rate/rhythm, respiration rate and rhythm, vibration responses in the lungs, and respiration volume. Others are also possible.

Figure 11A:
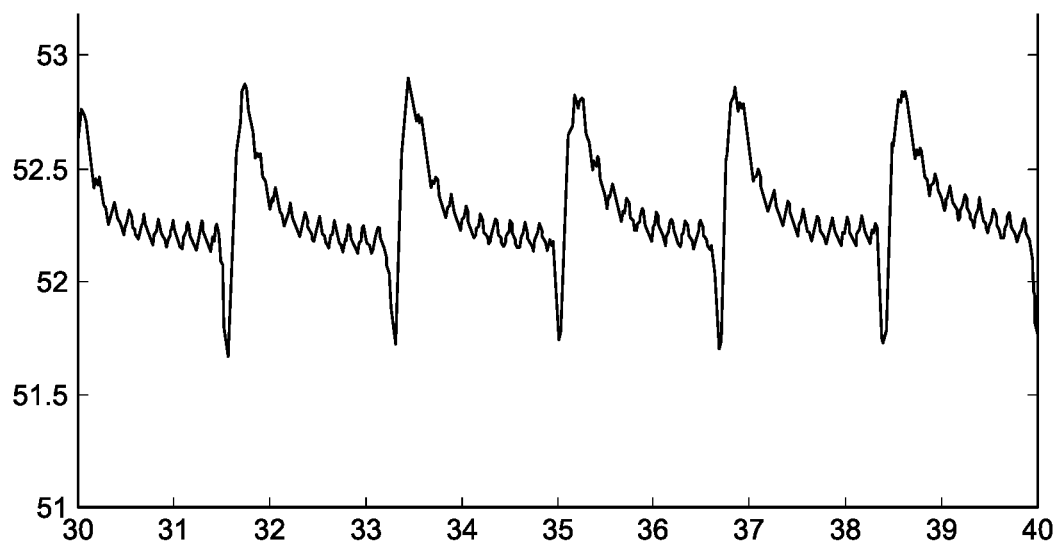
FIGS. 11A and 11B illustrate heart and lung activity of an anesthetized mouse, as detected by an embodiment of the physiological sensing device of FIG. 8.

FIG. 11A illustrates heart and lung activity of an anesthetized mouse, as detected by an embodiment of the physiological sensing device 800. In particular, FIG. 11A shows the heart beat and respiration of the mouse.

Due to the separable transmit waveforms and other techniques discussed herein and in U.S. patent application Ser. No. 15/478,179 (already incorporated by reference in its entirety), it is possible to linearly combine receiver signals with arbitrary complex weightings, thereby improving detection of desired phenomena. An example of linear weightings is shown in FIG. 11B.

Figure 11B:
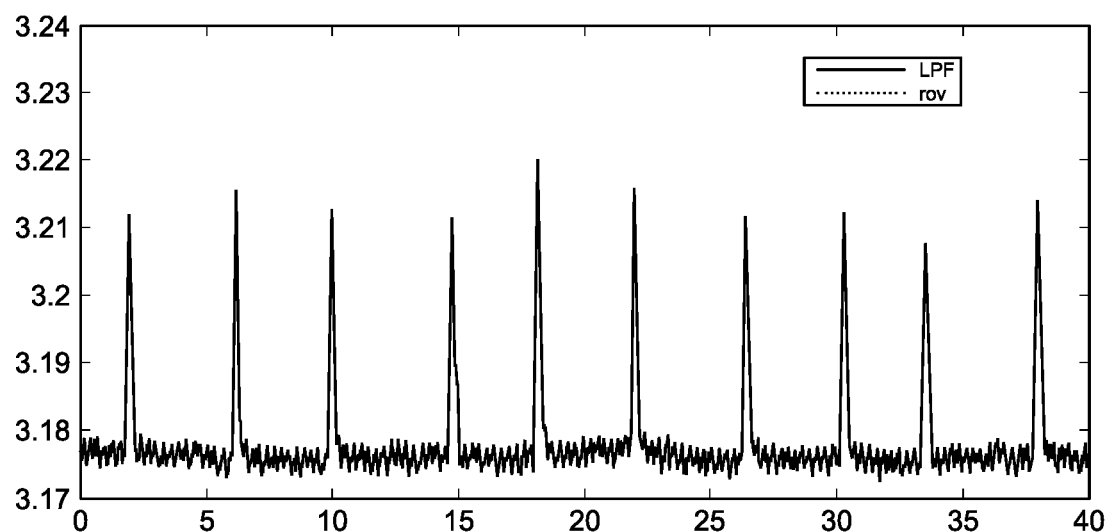

FIG. 11B shows how linear combinations of the received signals can accentuate certain aspects of the received signals. By applying a linear combination of received signals, such as the one illustrated in FIG. 11A, the plot in FIG. 11B accentuates the initiation of each respiration cycle.

CSD curves are believed to be dependent to a significant degree on the transmitter-channel-receiver system, including the state of any targets within the channel. (The CSD curves may be dependent to a lesser degree—potentially a far lesser degree—on the specific content or properties of the transmitted signals, for example, so long as the transmitted signals have adequate signal strength across the bandwidth being analyzed.) In other words, the CSD curves are believed to be strongly dependent on the factors impacting the transmitter (such as transmit antenna location/motion, transmit polarization, beam pattern, etc), the receiver (such as receiver antenna location/motion and beam pattern), and factors leading to the channel response. The CSD curves will change in response to physical changes in the frequency-selective environment, including physical movement of scatterer targets in relation to the locations of transmitting and receiving antennas. This means that characteristics of the CSD curves at a given moment in time may be used to identify a specific multipath channel, including a specific state of a target (e.g., patient or other subject) located in the channel, potentially without knowledge of the transmitted signal(s) that produced the CSD curves.

One application of this property is that the transmitted signal(s) need not necessarily be known in order to determine useful information about a target, such as a patient, located in the channel. Instead, a signal of opportunity (e.g., one which is transmitted by a device in the environment of the subject other than the physiological sensing device 800) can be used as the transmitted signal. In such embodiments, the physiological sensing device 800 need not necessarily include the transmitter 810 or the transmit antennas. Signals of opportunity could include, for example, cellular telephone signals, Wi-Fi signals from an Internet hotspot, a Bluetooth signal from a Bluetooth-enabled device, and many others. Another example of a signal of opportunity is one which is transmitted by a baby video monitor. These devices emit radio frequency signals that can be used by the physiological sensing device 800 to monitor the heart activity, lung activity, and/or motion activity of the baby (and/or the presence of nearby subjects). Another application is the use of the detected heart rate to discriminate a target. For example, an adult human heart rate versus a baby heart rate or fetal heart rate, or a rodent or a dog. This would be of interest in the baby monitoring application and perhaps also in perimeter security. These signals can be received and analyzed using the systems and techniques discussed herein to learn information about the heart or lung activity of a subject. Hospitals or other clinical environment may have strict regulations regarding the transmission of wireless signals. Thus, it could be advantageous if the physiological sensing device 800 did not require its own transmitter but could instead make use of existing signals of opportunity. The system could generate one or more CSD curves by receiving and processing those existing transmitted signals, as discussed herein. If the subject's heart or lungs are present in the propagation channel between the receiver and the unknown transmitted signals of opportunity, then one or more of the CSD curves will likely include information about the movements induced by heart or lung activities. This movement (such as heart rate or respiration rate or associated rhythms) can be determined by, for example, analyzing the frequency content of the CSD information.

The same property that makes RF waves effective for remote-sensing also has the potential to degrade its performance—pervasiveness. The effective sensing zone of the RF-based physiological sensing device will be dictated by the field of view of the antennas. Therefore, it would be advantageous for any detectable level of movement within this zone to be separable from the subject's heart and lung responses. This can be addressed in the following ways: 1) Through prudent physical deployment, for example placing the antennas near the subject to reduce or minimize the impact of interference; 2) Through digital signal processing, filter environment changes that are out of the passband associated with the rates to be detected; 3) In digital signal processing, leverage the coherence among the subchannels to filter-out unwanted responses and to elicit desired signals from the background noise; 4) Through the use of matched filter processing to reduce responses with different ranges (this is like bistatic radar).

The deployment of the physiological sensing device 800 could dramatically affect Army medicine as it may be implemented and applied throughout the four roles of care. In role 1 situations, the device 800 could provide critical information at several points of care. The first could be to assist combat medics that are treating and evaluating casualties on the battlefield and evacuating them to a battalion aid station (BAS). The device 800 can be modular (potentially hand-held) and fixed over litter-bound patients in the back of a Humvee ambulance. In this situation, medics would immediately know if a patient is entering cardiac arrest, without using an EKG that would be too cumbersome to deploy in a field situation. The same applies for use at the BAS, where an EKG would be similarly impractical. While non-invasive heart monitoring of patients will always be desirable, its use at the BAS would also facilitate triage in mass casualty situations. In role 2 medical treatment scenarios, the device 800 could aid medics and physician assistants operating their respective "clinics," and could particularly help surgeons deployed with forward surgical teams (FSTs). If a surgeon is able to begin operating 60 to 120 seconds faster by using the device 800 rather than setting up an EKG, then that would enable more effective, and in some cases life-saving, care. In role 3 and role 4 medical care scenarios, the device 800 could serve a complimentary role to the EKG during surgery. It could also serve a unique new function in broad based heart monitoring of patients in holding areas. For example, if a rare but significant cardiac event happens to a patient in a holding area of a Combat Support Hospital, the device 800 could detect and alert medical staff. In summary, the physiological sensing device 800 could have a dramatic impact on Army medicine and ultimately assist in the effective treatment of battlefield casualties as they route through the roles of medical care.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps may be altered, added, removed, or rearranged. While certain embodiments have been explicitly described, other embodiments will become apparent to those of ordinary skill in the art based on this disclosure.

The systems and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a person of ordinary skill in the art will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers. In addition, where methods are described that are, or could be, at least in part carried out by computer software, it should be understood that such methods can be provided on non-transient computer-readable media (e.g., optical disks such as CDs or DVDs, hard disk drives, flash memories, diskettes, or the like) that, when read by a computer or other processing device, cause it to carry out the method.

A person of ordinary skill in the art will also appreciate, in light of this disclosure, that multiple distributed computing devices can be substituted for any one computing device illustrated herein. In such distributed embodiments, the functions of the one computing device are distributed such that some functions are performed on each of the distributed computing devices.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. A method for sensing a physiological characteristic of a subject, the method comprising:
   providing, in proximity to one or more portions of the subject's body, at least three antennas, comprising at least one transmitter antenna and at least one receiver antenna, wherein at least one of the antennas comprises a pair of substantially orthogonally-polarized antennas configured to enable characterization of the combined signal of at least one line of sight (LOS) signal and at least one multipath signal based on their polarization states for physiological sensing;
   coherently obtaining, at the at least one receiver antenna, obtained signals comprising the at least one LOS signal and the at least one multipath signal, wherein propagation of the at least one multipath signal involves one or more of reflection, diffraction, or scattering by or through the one or more portions of the subject's body, and wherein the coherent obtainment comprises use of a synchronized clock and a local oscillator in a plurality of channels at both the at least one transmitter antenna and the at least one receiver antenna, wherein the coherently obtaining maintains phase coherence between the transmitted signal and the obtained signals across a plurality of sub-bands, enabling accurate comparison of amplitude and phase information;
   determining the amplitude and phase information of the plurality of sub-bands for each of the obtained signals by transforming each of the obtained signals into a frequency domain; and determining comparison values by analyzing the amplitude and phase differences between received signal components and corresponding transmitted signal components, and using these values to calculate Jones vectors or Stokes parameters for the plurality of sub-bands;
   determining polarization information based on the comparison values, wherein the polarization information is derived from the calculated Jones vectors or Stokes parameters, and further characterizes the physiological characteristics of the subject, thereby enabling enhanced sensing of physiological characteristics.

2. The method of claim 1, wherein the signals comprise a signal transmitted by a device in an environment of the subject other than a physiological sensing device.

3. The method of claim 1, wherein a provision of the at least one transmitter antenna is in proximity to at least one of the one or more portions of the subject's body to provide at least one of the obtained signals.

4. The method of claim 1, further comprising: analyzing the physiological characteristic of the subject using the polarization information.

5. The method of claim 4, further comprising: identifying a characteristic of the polarization information at a given time or identifying a time-varying change in the polarization information.

6. The method of claim 4, further comprising: controlling a medical device based on the physiological characteristic.

7. The method of claim 1, wherein the one or more portions of the subject's body comprise a thorax.

8. The method of claim 1, wherein the one or more portions of the subject's body comprise a limb.

9. The method of claim 1, wherein the physiological characteristic of the subject is associated with heart or lung activity.

10. The method of claim 1, wherein the physiological characteristic of the subject is associated with movement of the subject's body.

11. The method of claim 1, further comprising: calculating correlations of the polarization information, being time-varying, to identify timing response differences due to heart responses from different parts of the subject's body to obtain pulse delay information.

12. The method of claim 1, further comprising: determining whether the subject is a human by comparing the polarization information to one or more criteria.

13. The method of claim 1, wherein the coherent obtainment of the signals comprises performing synchronous digital sampling of the signals.

14. The method of claim 1, wherein the signals are obtained using co-polarized portions of one or more receiver antennas.

15. The method of claim 1, wherein the at least one receiver antenna comprises a pair of orthogonally-polarized antennas and wherein the signals are obtained using the pair of orthogonally-polarized antennas.

16. The method of claim 1, wherein the obtained signals are respectively related to first and second transmitter signals, and wherein the obtained signals are separable in time, frequency, code, beam, or polarization.

17. The method of claim 16, wherein the obtained signals are coherently synthesized.

18. The method of claim 16, wherein the obtained signals overlap in time.

19. The method of claim 16, wherein the at least one receiver antenna comprises a pair of orthogonally-polarized antennas and the signals are sent using the pair of orthogonally-polarized antennas.

20. The method of claim 16, wherein the signals are sent using spatially-separated transmitter antennas.

21. The method of claim 1, wherein at least one of the signals is related to a transmitter signal.

22. The method of claim 1, further comprising: comparing respective frequency component phases and respective frequency component amplitudes of the obtained signals by calculating Jones vectors or Stokes parameters.

23. The method of claim 1, wherein the signals comprise radio frequency (RF) signals.

24. A system for monitoring a physiological characteristic of a subject, the system comprising:
   at least three antennas, including at least one transmitter antenna and at least one receiver antenna, wherein at least one of the antennas comprises a pair of substantially orthogonally-polarized antennas configured to enable characterization of the combined signal of at least one line of sight (LOS) signal and at least one multipath signal based on their polarization states for physiological sensing; and a processor configured to:
coherently obtain, at the at least one receiver antenna, obtained signals comprising the at least one LOS signal and the at least one multipath signal, wherein propagation of the at least one multipath signal involves one or more of reflection, diffraction, or scattering by or through at least a portion of the subject's body, and wherein the coherent obtainment comprises use of a synchronized clock and a local oscillator in a plurality of channels at both the at least one transmitter antenna and the at least one receiver antenna, wherein the coherently obtaining maintains phase coherence between the transmitted signal and the obtained signals across a plurality of sub-bands, enabling accurate comparison of amplitude and phase information;
determine the amplitude and phase information of the plurality of sub-bands for each of the obtained signals by transforming each of the obtained signals into a frequency domain; and
determine comparison values by analyzing the amplitude and phase differences between received signal components and corresponding transmitted signal components, and using these values to calculate Jones vectors or Stokes parameters for the plurality of sub-bands;
determine polarization information based on the comparison values, wherein the polarization information is derived from the calculated Jones vectors or Stokes parameters, and further characterizes the physiological characteristics of the subject, thereby enabling enhanced sensing of physiological characteristics.

25. The system of claim 24, wherein the signals comprise a signal transmitted by a device in an environment of the subject other than a physiological sensing device.

26. The system of claim 24, wherein the system is monostatic.

27. The system of claim 24, wherein the system is bistatic.

28. The system of claim 24, wherein the processor is further configured to analyze the physiological characteristic of the subject using the polarization information.

29. The system of claim 24, wherein the processor is further configured to analyze the physiological characteristic of the subject by identifying a characteristic of a curve formed from the polarization information at a given time or identifying a time-varying change in the polarization information.

30. The system of claim 24, wherein at least one of the at least one transmitter antenna or the at least one receiver antenna is integrated into a bed or chair.

31. The system of claim 24, further comprising: a common local oscillator to frequency down-convert the obtained signals, and one or more analog-to-digital converters to perform synchronous digital sampling of the signals.

32. The system of claim 24, further comprising: transmitter circuitry to coherently synthesize first and second transmitter signals.

33. The system of claim 24, wherein the at least one transmitter antenna comprises a plurality of transmitter antennas.

34. The system of claim 24, wherein the at least one receiver antenna comprises a plurality of receiver antennas.

35. The method of claim 1, wherein the at least one receiver antenna comprises spatially-separated and orthogonally-polarized antennas.

36. The system of claim 24, wherein the at least one receiver antenna comprises spatially-separated and orthogonally-polarized antennas.

37. The method of claim 1, wherein the signals comprise electromagnetic frequency bands, including optical, infrared, ultraviolet, or x-ray signals.

38. The system of claim 24, wherein the signals comprise electromagnetic frequency bands, including optical, infrared, ultraviolet, or x-ray signals.

39. The method of claim 1, wherein the received signals are processed by pairing the transmitted signals and corresponding received signals, the pairing comprising:
comparing the amplitude and phase differences between the transmitter-receiver signal pairs, including the LOS signals and multipath signals, wherein the transmitted signals are transmitted via dual-polarized antennas and the received signals are captured by dual-polarized receiver antennas, and
wherein the determining the amplitude and phase information of the plurality of sub-bands for each of the obtained signals by transforming each of the obtained signals into a frequency domain comprises transforming the paired signals into the frequency domain and analyzing the amplitude and phase information of each paired signal across the plurality of sub-bands to calculate Jones vectors or Stokes parameters corresponding to a polarization state.

40. The system of claim 24, wherein the received signals are processed by pairing the transmitted signals and corresponding received signals, the pairing comprising:
comparing the amplitude and phase differences between the transmitter-receiver signal pairs, including the LOS signals and multipath signals, wherein the transmitted signals are transmitted via dual-polarized antennas and the received signals are captured by dual-polarized receiver antennas, and
wherein the determining the amplitude and phase information of the plurality of sub-bands for each of the obtained signals by transforming each of the obtained signals into a frequency domain comprises transforming the paired signals into the frequency domain and analyzing the amplitude and phase information of each paired signal across the plurality of sub-bands to calculate Jones vectors or Stokes parameters corresponding to a polarization state.

* * * * *